(12) United States Patent
Kim et al.

(10) Patent No.: US 10,456,039 B2
(45) Date of Patent: Oct. 29, 2019

(54) ELECTRONIC APPARATUS, SYSTEM, AND CONTROL METHOD THEREOF

(71) Applicant: SAMSUNG ELECTRONICS CO., LTD., Suwon-si (KR)

(72) Inventors: Seoung-hun Kim, Hwaseong-si (KR); Sung-chan Ko, Seoul (KR); Hyun-woo Koh, Yongin-si (KR); Min-gu Lee, Hwaseong-si (KR); Seung-bin Im, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/341,450

(22) Filed: Nov. 2, 2016

(65) Prior Publication Data

US 2017/0119252 A1    May 4, 2017

(30) Foreign Application Priority Data

Nov. 2, 2015    (KR) .......................... 10-2015-0153347
Mar. 10, 2016    (KR) .......................... 10-2016-0029058

(51) Int. Cl.
*A61B 5/00*        (2006.01)
*A61B 5/0205*      (2006.01)
(Continued)

(52) U.S. Cl.
CPC ........ *A61B 5/0024* (2013.01); *A61B 5/02055* (2013.01); *A61B 5/0404* (2013.01);
(Continued)

(58) Field of Classification Search
CPC ............. G06F 19/3406; G06F 19/3418; A61B 2562/225; A61B 2562/226;
(Continued)

(56) References Cited

U.S. PATENT DOCUMENTS 5,963,650 A * 10/1999 Simionescu ........... G01D 4/004
                                                       340/870.02
7,953,613 B2    5/2011 Gizewski
(Continued)

FOREIGN PATENT DOCUMENTS

CN         204272234 U     4/2015
EP         2 898 822 A1    7/2015
(Continued)

OTHER PUBLICATIONS

International Search Report (PCT/ISA/210) dated Feb. 20, 2017 issued by the International Searching Authority in counterpart International Application No. PCT/KR2016/012415.
(Continued)

*Primary Examiner* — Franklin D Balseca
(74) *Attorney, Agent, or Firm* — Sughrue Mion, PLLC

(57) ABSTRACT

An electronic apparatus includes: a connector which is configured to enable one of measurement devices for measuring different types of bio signals to be selectively attached thereto or detached therefrom; a communication device configured to communicate with an external apparatus; and a processor configured to, in response to the measurement device being attached to the connector, obtain identification information of the attached measurement device and transmit the identification information to the external apparatus, and control the attached measurement device based on a control command received from the external apparatus.

10 Claims, 30 Drawing Sheets

(51) Int. Cl.
*A61B 5/0404* (2006.01)
*A61B 5/145* (2006.01)
*A61B 7/04* (2006.01)
*H04Q 9/00* (2006.01)

(52) U.S. Cl.
CPC ........ *A61B 5/14532* (2013.01); *A61B 5/6898* (2013.01); *A61B 5/72* (2013.01); *A61B 5/742* (2013.01); *A61B 7/04* (2013.01); *A61B 2560/0214* (2013.01); *A61B 2562/226* (2013.01); *A61B 2562/227* (2013.01); *H04Q 9/00* (2013.01); *H04Q 2209/00* (2013.01)

(58) Field of Classification Search
CPC ...... A61B 2562/227; A61B 2560/0214; A61B 2560/0443; A61B 2560/045; A61B 5/0432; A61B 5/044; A61B 5/72; A61B 5/0024; A61B 5/02055; A61B 5/0404; A61B 5/14532; A61B 5/742; A61B 7/04; H04Q 220/00; H04Q 220/10; H04Q 220/40; H04Q 220/43; H04Q 220/47; H04Q 220/80; H04Q 9/00; H04Q 2209/00; H04Q 2209/10; H04Q 2209/40; H04Q 2209/43; H04Q 2209/47; H04Q 2209/80
See application file for complete search history.

(56) References Cited

U.S. PATENT DOCUMENTS

| | | | |
|---|---|---|---|
| 8,554,921 B2 | 10/2013 | Hannemann et al. | |
| 8,823,490 B2 | 9/2014 | Libbus et al. | |
| 9,398,852 B2* | 7/2016 | Enomoto | A61B 5/0006 |
| 9,986,919 B2* | 6/2018 | Lamego | A61B 5/02141 |
| 2001/0038343 A1* | 11/2001 | Meyer | G01D 4/004 |
| | | | 340/870.02 |
| 2007/0038883 A1 | 2/2007 | Gerder et al. | |
| 2009/0270743 A1 | 10/2009 | Dugan et al. | |
| 2010/0130873 A1* | 5/2010 | Yuen | A61B 5/0205 |
| | | | 600/484 |
| 2011/0213225 A1* | 9/2011 | Bernstein | G06Q 50/22 |
| | | | 600/309 |
| 2014/0159921 A1 | 6/2014 | Qualey et al. | |
| 2014/0375428 A1* | 12/2014 | Park | G06K 7/10237 |
| | | | 340/10.1 |
| 2015/0035643 A1 | 2/2015 | Kursun | |
| 2016/0183836 A1* | 6/2016 | Muuranto | A61B 5/04288 |
| | | | 600/301 |
| 2016/0321420 A1* | 11/2016 | Klee | A61M 16/06 |
| 2017/0055848 A1* | 3/2017 | Hughes | A61B 5/02141 |
| 2017/0102294 A1* | 4/2017 | Beeke | G01D 21/02 |
| 2017/0337339 A1* | 11/2017 | Cronin | G16H 50/30 |

FOREIGN PATENT DOCUMENTS

| | | |
|---|---|---|
| JP | 10-328147 A | 12/1998 |
| KR | 10-2005-0042964 A | 5/2005 |
| KR | 10-0894545 B1 | 4/2009 |
| KR | 10-2012-0019940 A | 3/2012 |
| KR | 10-1146900 B1 | 5/2012 |
| KR | 10-2015-0067047 A | 6/2015 |
| WO | 2012/067318 A1 | 5/2012 |

OTHER PUBLICATIONS

Written Opinion (PCT/ISA/237) dated Feb. 20, 2017 issued by the International Searching Authority in counterpart International Application No. PCT/KR2016/012415.

\* cited by examiner

ELECTRONIC APPARATUS, SYSTEM, AND CONTROL METHOD THEREOF

CROSS-REFERENCE TO RELATED APPLICATIONS

This application claims priority from Korean Patent Application No. 10-2015-0153347, filed on Nov. 2, 2015, and Korean Patent Application No. 10-2016-0029058, filed on Mar. 10, 2016, in the Korean Intellectual Property Office, the disclosure of which are incorporated herein by reference in their entireties.

BACKGROUND

Field

Apparatuses and methods consistent with exemplary embodiments relate to an electronic apparatus, a system, and a control method thereof, and more particularly, to an electronic apparatus and a system for measuring a bio signal and diagnosing, and a control method thereof.

Description of the Related Art

With the development of electronic technology, various kinds of electronic products have been developed and widely distributed. In particular, various display apparatuses such as a television (TV), a mobile phone, a personal computer (PC), a notebook PC, a personal digital assistant (PDA), are increasingly used in general households. In addition, various electronic devices are provided with functions of measuring a user's bio signal and diagnosing a user's health state based on the bio signal.

In particular, such diagnostic devices are standalone devices which are manufactured according to an object to be measured and a type of bio signal.

However, some of the standalone devices are not provided with a communication function, and, even if the devices are able to perform a communication function, the devices use different software. Therefore, the user need to buy, maintain, and manage each kind of diagnostic device separately and also need to individually manage software corresponding to each diagnostic device, which causes inconvenience.

SUMMARY

One or more exemplary embodiments may overcome the above disadvantages and other disadvantages not described above. However, an exemplary embodiment is not required to overcome the disadvantages described above, and may not overcome any of the problems described above.

One or more exemplary embodiments provide an electronic apparatus which enables one of a plurality of measurement modules for measuring different types of bio signals to be selectively attached thereto and detached therefrom, a system, and a control method thereof.

According to an aspect of an exemplary embodiment, there is provided an electronic apparatus including: a connector which is configured to enable one of a plurality of measurement modules for measuring different types of bio signals to be selectively attached thereto and detached therefrom; a communication device configured to communicate with an external apparatus; and a processor configured to, in response to one of the plurality of measurement modules being attached to the connector, obtain identification information of the measurement module attached to the connector and transmit the identification information to the external apparatus, and control the measurement module attached to the connector based on a control command received from the external apparatus.

Each of the plurality of measurement modules may include a different sensor according to a type of a bio signal to be measured.

In response to a control command for starting measuring the bio signal being received from the external apparatus which has received an identification number of the measurement module attached to the connector, the processor may be configured to drive the measurement module attached to the connector and start measuring the bio signal, and, in response to a control command for stopping measuring the bio signal being received from the external apparatus, the processor may be configured to drive the measurement module attached to the connector and stop measuring the bio signal.

The electronic apparatus may further include a battery, and the processor may be configured to convert power charged in the battery into a driving voltage for the measurement module attached to the connector, and provide the driving voltage to the measurement module attached to the connector.

In response to the measurement module attached to the connector being changed another measurement module and a driving voltage of the changed another measurement module being different from the driving voltage of the previous measurement module, the processor may be configured to convert the power charged in the battery into the driving voltage of the changed another measurement module and provide the driving voltage to the changed another measurement module.

The communication device may include a near-field communication (NFC) tagger and a Bluetooth communication device, and, in response to the electronic apparatus and the external apparatus being adjacent to each other within a predetermined range, the processor may be configured to exchange information for Bluetooth communication pairing with the external apparatus via the NFC tagger, and, in response to the Bluetooth communication pairing being completed, transmit the identification information of the measurement module attached to the connector to the external apparatus via the Bluetooth communication device.

The electronic apparatus may further include a display, and the processor may be configured to display information on a state of the electronic apparatus through the display.

The information on the state of the electronic apparatus may include at least one piece of information of information on an operation state of the electronic apparatus, an amount of power charged in the battery, and whether the battery is charged or not.

The connector may include a connection terminal for connecting with one of the plurality of measurement modules, and the processor may be configured to transmit the driving voltage of the measurement module attached to the connector and the control command to the measurement module attached to the connector via the connection terminal, and receive information on the bio signal from the measurement module attached to the connector via the connection terminal.

According to an aspect of an exemplary embodiment, there is provided a system which includes an electronic apparatus which enables one of a plurality of measurement modules for measuring different types of bio signals to be selectively attached thereto and detached therefrom, and a user terminal apparatus for controlling the electronic apparatus, the system including: the electronic apparatus which is configured to, in response to one of the plurality of measurement modules being connected, obtain identification information of the connected measurement module and transmit the identification information to the user terminal apparatus; and the user terminal apparatus which is configured to display a user interface screen corresponding to the connected measurement module based on the identification information of the connected measurement module, which is received from the electronic apparatus, and transmit a control command input through the user interface screen to the electronic apparatus, wherein the electronic apparatus is configured to control the connected measurement module based on the received control command.

In response to information on a bio signal measured by the measurement module connected to the electronic apparatus being received, the user terminal apparatus may be configured to analyze the received information and display a result of the analyzing on the user interface screen.

According to an aspect of an exemplary embodiment, there is provided a control method of an electronic apparatus which includes a connector configured to enable one of a plurality of measurement modules for measuring different types of bio signals to be selectively attached thereto and detached therefrom, the method including: in response to one of the plurality of measurement modules being attached to the connector, obtaining identification information of the measurement module attached to the connector and transmitting the identification information to an external apparatus; and controlling the measurement module connected to the connector based on a control command received from the external apparatus.

Each of the plurality of measurement modules may include a different sensor according to a type of a bio signal to be measured.

The controlling may include, in response to a control command for starting measuring the bio signal being received from the external apparatus which has received an identification number of the measurement module attached to the connector, driving the measurement module attached to the connector and starting measuring the bio signal, and, in response to a control command for stopping measuring the bio signal being received from the external apparatus, driving the measurement module attached to the connector and stopping measuring the bio signal.

The controlling may include converting power charged in a battery included in the electronic apparatus into a driving voltage for the measurement module attached to the connector, and providing the driving voltage to the measurement module attached to the connector.

The transmitting may include, in response to the electronic apparatus and the external apparatus being adjacent to each other within a predetermined range, exchanging information for Bluetooth communication pairing with the external apparatus through NFC tagging, and, in response to the Bluetooth communication pairing being completed, transmitting the identification information of the measurement module attached to the connector to the external apparatus through the Bluetooth communication.

The control method may further include displaying information on a state of the electronic apparatus.

The information on the state of the electronic apparatus may include at least one piece of information of information on an operation state of the electronic apparatus, an amount of power charged in a battery, and whether the battery is charged.

The connector may include a connection terminal for connecting with one of the plurality of measurement modules, and the control method may further include: transmitting the driving voltage of the measurement module attached to the connector and the control command to the measurement module attached to the connector via the connection terminal; and receiving information on the bio signal from the measurement module attached to the connector via the connection terminal.

According to another aspect of exemplary embodiment, there is provided a mobile device which includes a body which houses the mobile device, a connector which is disposed on a surface of the body and made common to be connected to different types of measurement devices, each of the measurement devices including a different sensing device being configured to measure bio signals different from one another and a processor configured to, in response to one of the measurement devices being attached to the connector, obtain identification information of the attached measurement device, and control the attached measurement device to measure the bio signal based on the obtained identification information.

The processor may supply voltage of different levels to the measurement devices through the connector, to support the different types of the sensing devices.

According to various exemplary embodiments, various measurement modules may be selectively attached to the electronic apparatus and used, and the electronic apparatus includes common elements included in various measurement modules, such that a diagnostic device can be miniaturized and a price thereof can be reduced.

BRIEF DESCRIPTION OF THE DRAWINGS

The above and/or other aspects will become more apparent by describing certain exemplary embodiments, with reference to the accompanying drawings, in which.

DETAILED DESCRIPTION OF THE EXEMPLARY EMBODIMENTS

Figure 1:
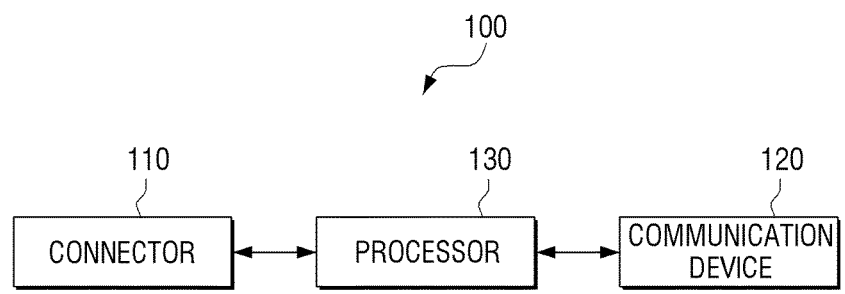
FIG. 1 is a block diagram showing a configuration of an electronic apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

FIG. 1 is a block diagram showing a configuration of an electronic apparatus according to an exemplary embodiment.

Referring to FIG. 1, the electronic apparatus 100 may include a connector 110, a communication device 120, and a processor 130. Specifically, the electronic apparatus 100 refers to an apparatus which performs a common operation regardless of the type of measurement module, i.e., a measurement device, and performs functions of supplying power to a measurement module or receiving a bio signal measured by a measurement module and transmitting the bio signal to an external apparatus, e.g., a user terminal or a user device. Such an electronic apparatus 100 enables various measurement modules to be attached thereto and detached therefrom and may be implemented in various forms.

The connector 110 is implemented to enable one of a plurality of measurement modules for measuring different types of bio signals to be selectively attached thereto and detached therefrom. Specifically, the connector 110 has a structure to be physically engaged with a connector provided in the measurement module, and the connector 110 may include a connection terminal to supply power or transmit and receive data to and from the connected measurement module. For example, as a connector provided in a measurement module and a connector provided in a body of the electronic apparatus are engaged with each other and connected, the measurement module and the electronic apparatus 100 may be connected with each other. The connector 110 may be connected with the connector provided in the measurement module by a connection method through magnetic force using a magnetic substance as well as the method using the physical structure. However, this is not limiting and the connectors may be connected with each other in various ways. The connection method using magnetic force will be described below in detail.

Each of the plurality of measurement modules may include a different sensor according to the type of bio signal to be measured. Specifically, each of the plurality of measurement modules may be implemented in a different form according to the type of bio signal to be measured, and may be implemented in a different form according to a bio signal to be measured, and may include a sensor according to the type of bio signal to be measured. That is, there are different types of measurement modules according to types of various bio signals.

For example, when the bio signal to be measured is related to an electrocardiogram (ECG), the measurement module may include a sensor to do the ECG. When the bio signal to be measured is related to body temperature, the measurement module may include a sensor to measure body temperature. When the bio signal to be measured is related to blood glucose, the measurement module may include a sensor to measure blood glucose.

The bio signal refers to an electric signal between micro cells of the body, and may include, but not limited to, brainwaves, an electromyogram, a heart rate, a breathing rate, stability and change in an emotional state, or the like, in addition to the above-described ECG, body temperature, and blood glucose.

A measurement module including a different sensor according to the type of bio signal may be implemented.

The communication device 120 may communicate with an external apparatus. The external apparatus refers to an electronic apparatus which performs functions of receiving the bio signal measured by the measurement module, analyzing the bio signal and diagnosing the patient, and displaying and storing the result of the diagnosing. For example, the external apparatus may include at least one among a TV, a notebook PC, a tablet, a desktop PC, a set-top box, a game console, a mobile phone, or the like.

The communication device 120 may communicate with the external apparatus in various communication methods, and may communicate with the external apparatus in a communication method such as Bluetooth (BT), Wireless Fidelity (WiFi), Zigbee, Infrared (IR), Serial Interface, a Universal Serial Bus (USB), Near Field Communication (NFC), or the like.

In response to one of the plurality of measurement modules being attached to the connector 110, the processor 130 may obtain identification information of the measurement module attached to the connector 110 and transmit the identification information to the external apparatus, and may control the measurement module attached to the connector 110 based on a control command received from the external apparatus.

Specifically, the plurality of measurement modules have different identification information, and, in response to one of the plurality of measurement modules being attached to the connector 110, the processor 130 may obtain the identification information from the measurement module attached to the connector 110. The processor 130 may transmit the obtained identification information to the external apparatus via the communication device 120.

Accordingly, the external apparatus may determine which of the measurement modules is attached to the electronic apparatus 100 based on the received identification information, and may execute software for driving the determined measurement module.

In response to a user manipulation for controlling the measurement module attached to the electronic apparatus 100 being input in the state in which the software is executed, the external apparatus may transmit a control command corresponding to the input user manipulation to the electronic apparatus 100.

The processor 130 may control the measurement module attached to the connector 110 based on the control signal received from the external apparatus.

Specifically, in response to a control command to start measuring the bio signal being received from the external apparatus which has received the identification number of the measurement module attached to the connector 110, the processor 130 may drive the measurement module attached to the connector 110 and start measuring the bio signal, and, in response to a control command to stop measuring the bio signal being received from the external apparatus, the processor 130 may drive the measurement module attached to the connector 110 and stop measuring the bio signal.

For example, when the measurement module attached to the connector 110 is a measurement module for measuring body temperature, the processor 130 may transmit the identification number of the measurement module attached to the connector 110 to the external apparatus, and the external apparatus may determine that the measurement module attached to the electronic apparatus 100 is the measurement module for measuring body temperature based on the received identification number.

The external apparatus may execute software for driving the measurement module for measuring body temperature, and display a user interface screen corresponding to the executed software.

The external apparatus may receive a user manipulation for controlling the measurement module on the displayed user interface screen, and the user manipulation may be a manipulation for the measurement module for measuring body temperature to start measuring body temperature or may be a manipulation for stopping measuring body temperature.

When the user manipulation is a manipulation for the measurement module for measuring body temperature to start measuring body temperature, the external apparatus may generate a control command to start measuring body temperature, and transmit the control command to the electronic apparatus 100, and accordingly, the processor 130 may drive the measurement module attached to the connector 110 to measure body temperature based on the received control command.

When the user manipulation is a manipulation for the measurement module for measuring body temperature to stop measuring body temperature, the external apparatus may generate a control command to stop measuring body temperature, and transmit the control command to the electronic apparatus 100, and accordingly, the processor 130 may drive the measurement module attached to the connector 110 to stop measuring body temperature based on the received control command.

The measurement module for measuring body temperature has been described as an example, but this is not limiting. The described-above may be applied to a measurement module for doing an ECG, a measurement module for measuring blood glucose, a measurement module for measuring blood pressure, or the like.

The identification information of the measurement module may include all types of information for identifying the measurement modules, in addition to the identification number. For example, when identification codes corresponding to the plurality of measurement modules for measuring different bio signals are stored in the external apparatus as a lookup table, the external apparatus may identify which measurement module is currently attached to the electronic apparatus 100 by comparing the identification code of the measurement module received via the electronic apparatus 100 and the lookup table.

Accordingly, the electronic apparatus 100 may be connected with various measurement modules, and the external apparatus may identify each of the various measurement modules connected to the electronic apparatus 100, and display the user interface screen corresponding to each of the identified measurement modules and provide the result of diagnosing.

According to an exemplary embodiment, the electronic apparatus 100 may further include a battery for supplying power for driving the electronic apparatus 100 and driving the measurement module attached to the connector 110.

Figure 2:
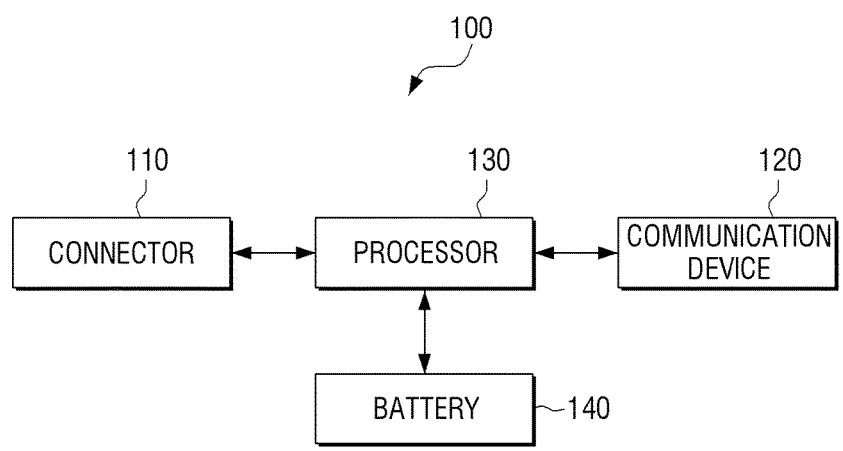
FIG. 2 is a block diagram showing a configuration of an electronic apparatus according to an exemplary embodiment.

FIG. 2 is a block diagram showing a configuration of an electronic apparatus according to an exemplary embodiment.

Referring to FIG. 2, the electronic apparatus 100 includes a connector 110, a communication device 120, a processor 130, and a battery 140.

The battery 140 may store power to supply power for driving the electronic apparatus 100 itself or driving a measurement module attached to the connector 110.

Specifically, the processor 130 may convert power charged in the battery 140 into a driving voltage for the measurement module attached to the connector 110, and provide the power to the measurement module attached to the connector.

For example, the processor 130 may use a circuit such as a DC-DC converter or a regulator to convert the power charged in the battery 140 into the driving voltage for the measurement module attached to the connector 110.

In response to the measurement module attached to the connector 110 being changed to another measurement module, and the driving voltage of another measurement module being different from the driving voltage of the previously-connected measurement module, the processor 130 may convert the power charged in the battery 140 into the driving voltage for another measurement module and provide the power to another measurement module.

For example, the measurement module currently attached to the connector 110 may be the measurement module for doing the ECG. In this state, in response to the measurement module attached to the connector 110 being changed to the measurement module for measuring body temperature by the user, the voltage for driving the measurement module for doing the ECG and the voltage for driving the measurement module for measuring body temperature may be different from each other. In this case, the processor 130 may convert the driving voltage into the driving voltage for the measurement module for measuring body temperature and provide the driving voltage to the measurement module for measuring the body temperature, instead of the voltage for driving the measurement module for the ECG.

Figure 3:
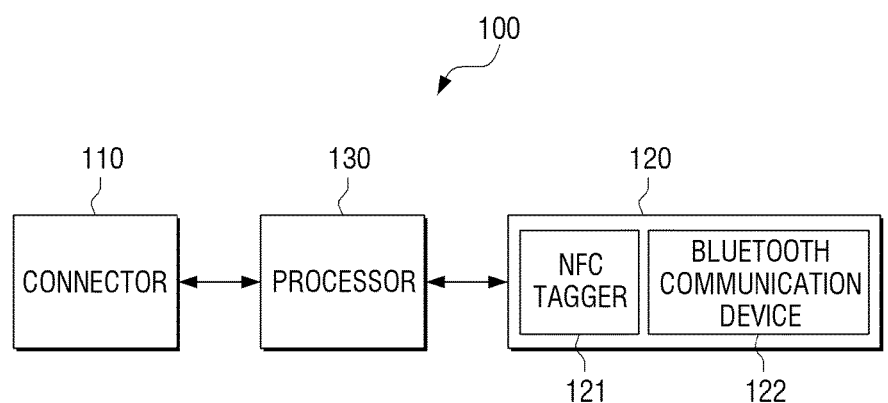
FIG. 3 is a view showing a detailed configuration of a communication device according to an exemplary embodiment.

FIG. 3 is a view illustrating a detailed configuration of the communication device according to an exemplary embodiment.

Referring to FIG. 3, the communication device 120 may include an NFC tagger 121 and a Bluetooth communication device 122.

In response to the electronic apparatus 100 and the external apparatus being adjacent to each other within a predetermined range, the processor 130 may exchange information for Bluetooth communication pairing with the external apparatus via the NFC tagger 121, and, in response to the Bluetooth communication pairing being completed, the processor 130 may transmit identification information of a measurement module attached to the connector 110 to the external apparatus via the Bluetooth communication device 122.

Specifically, in response to the electronic apparatus 100 and the external apparatus being close to each other and thus the NFC tagger 121 of the electronic apparatus 100 and the NFC tagger of the external apparatus being close to each other, the external apparatus may automatically recognize the electronic apparatus 100 and exchange information for Bluetooth communication pairing to establish a Bluetooth communication session with the electronic apparatus 100. In response to the information for Bluetooth communication pairing being exchanged and authentication being completed, the Bluetooth communication pairing may be completed and Bluetooth communication may be connected between the electronic apparatus 100 and the external apparatus. The Bluetooth communication is described as an example, but this is not limiting and various wireless communication methods such as WiFi, Zigbee, IR, or the like may be applied.

After the Bluetooth communication pairing is completed, the processor 130 may transmit the identification information of the measurement module attached to the connector 110 to the external apparatus via the Bluetooth communication device 122. Accordingly, the external apparatus may recognize the measurement module attached to the electronic apparatus 100 based on the received identification information.

Figure 4:
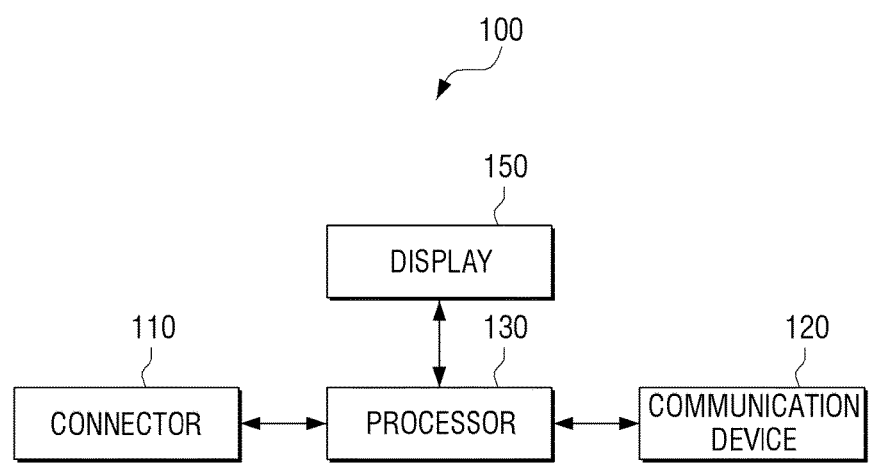
FIG. 4 is a block diagram showing a configuration of an electronic apparatus according to an exemplary embodiment.

FIG. 4 is a block diagram showing a configuration of an electronic apparatus according to an exemplary embodiment.

Referring to FIG. 4, the electronic apparatus 100 may include a connector 110, a communication device 120, a processor 130, and a display 150.

The processor 130 may display information on the state of the electronic apparatus 100 through the display 150.

The information on the state of the electronic apparatus 100 may include at least one piece of information on the operation state of the electronic apparatus 100, an amount of power charged in the battery 140, and whether the battery 140 is charged.

The display 150 may have a screen which is able to display an object, and may, for example, include at least one light emitting diode (LED).

For example, when the display 150 includes the LED, the processor 130 may indicate whether the electronic apparatus 100 is being driven or not using color of the LED. In response to the electronic apparatus 100 being currently driven, the processor 130 may control the LED to emit light of blue color, and, in response to the electronic apparatus 100 not being driven, the processor 130 may turn off the LED.

In response to the amount of power charged in the battery 140 being less than or equal to a predetermined value, the processor 130 may control the LED to emit light of red color or to flicker in a predetermined pattern.

In response to the electronic apparatus 100 being currently charged, the processor 130 may control the LED to emit light of yellow color in order to indicate that the electronic apparatus 100 is being charged. In response to the battery 140 being fully charged, the processor 130 may control the LED to emit light of green color.

However, the above-described colors and the displaying order are not limiting.

The connector 110 may include a connection terminal for connecting to one of the plurality of measurement modules, and the processor 130 may transmit a driving voltage for the measurement module attached to the connector 110 and a control command to the measurement module attached to the connector 110 via the connection terminal, and may receive information on a bio signal from the measurement module attached to the connector 110.

Specifically, the connector 110 may include a connection terminal of a predetermined standard form, and, in response to one of the plurality of measurement modules being attached to the connector 110, the processor 130 may provide a driving voltage to the measurement module via the connection terminal provided in the connector 110, and may transmit data including a control command received from the external apparatus to the measurement module. The processor 130 may receive information on a bio signal measured by the measurement module and identification information of the measurement module via the connection terminal provided in the connector 110.

Figure 5:
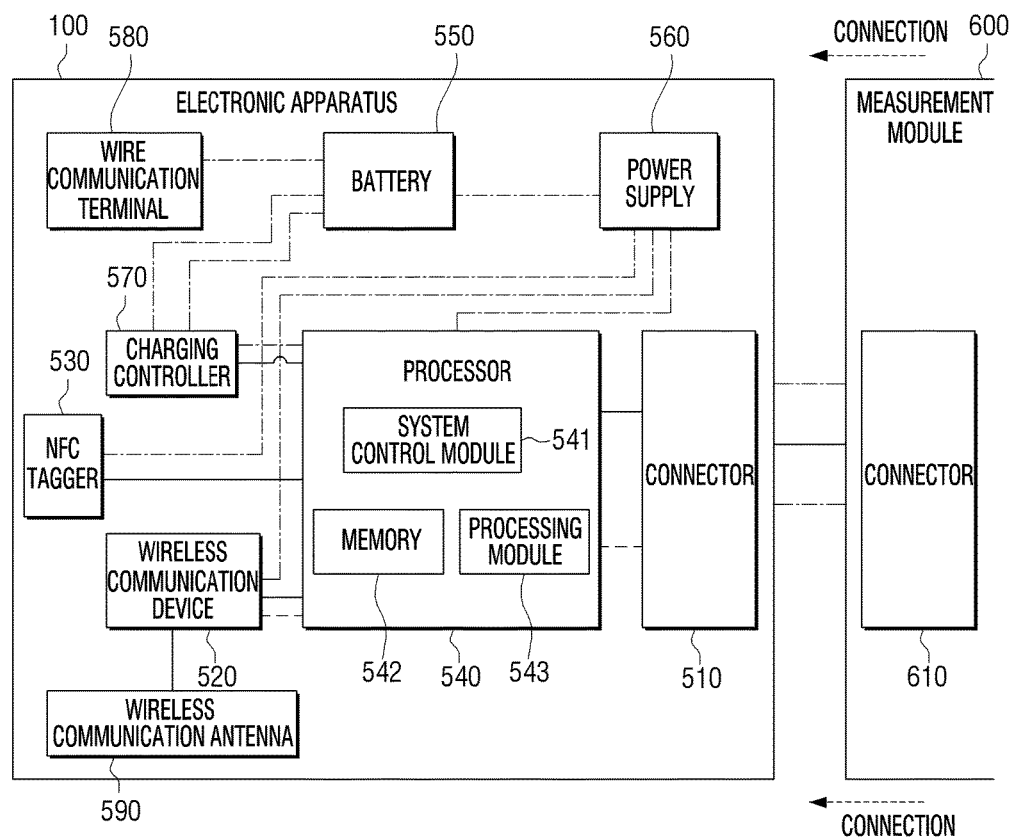
FIG. 5 is a view showing a detailed configuration of an electronic apparatus according to an exemplary embodiment.

FIG. 5 is a view showing a detailed configuration of an electronic apparatus according to an exemplary embodiment.

Referring to FIG. 5, the electronic apparatus 100 may include a connector 510, a wireless communication device 520, an NFC tagger 530, a processor 540, a battery 550, a power supply 560, a charging controller 570, a wire communication terminal 580, and a wireless communication antenna 590. The NFC tagger 530 and the wireless communication device 520 may correspond to the NFC tagger 121 and the Bluetooth communication device 122 described in FIG. 3, respectively, and may perform the same operations.

The connector 510 may correspond to the connector 110 described in FIG. 1, and may be a physical connection structure to be attached to a connector 610 of a measurement module 600 which is one of a plurality of measurement modules 608 (see FIG. 7) that can be connected to the electronic apparatus 100 via the same connector 510. The connector 510 may be used to provide a driving voltage to the measurement module 600 attached thereto or exchange a control command, information on a bio signal, or identification information of the measurement module 600.

As described above, in response to one of a plurality of measurement modules being attached to the connector 510, the processor 540 may obtain identification information of the measurement module attached to the connector 510 and transmit the identification information to an external apparatus, and may control the measurement module attached to the connector 510 based on a control command received from the external apparatus. In relation to this, the processor 540 may include a system control module 541, a memory 542, and a processing module 543.

The system control module 541 is a control module for driving the electronic apparatus 100, and the processing module 543 is a module for processing identification information received from the measurement module in a data form or processing a control command received from the external apparatus in a data form for driving the measurement module.

The memory 542 may store the identification information received from the measurement module, and also, may store an overall program for controlling the electronic apparatus 100.

The wireless communication device 520 may communicate in various wireless communication methods such as WiFi, Zigbee, IR, or the like, in addition to Bluetooth. The wireless communication device 520 may wirelessly communicate via the wireless communication antenna 590.

The battery 550 may correspond to the battery 140, and the charging controller 570 for charging the battery 550 may be included in the electronic apparatus 100, and the wire communication terminal 580 including a terminal for receiving power for charging the battery 550 from an external power source may be included. The processor 540 may use an amount of power stored in the battery 550 to drive the electronic apparatus 100 through the power supply 560, and/or may provide a driving voltage to the measurement module 600.

Figure 6:
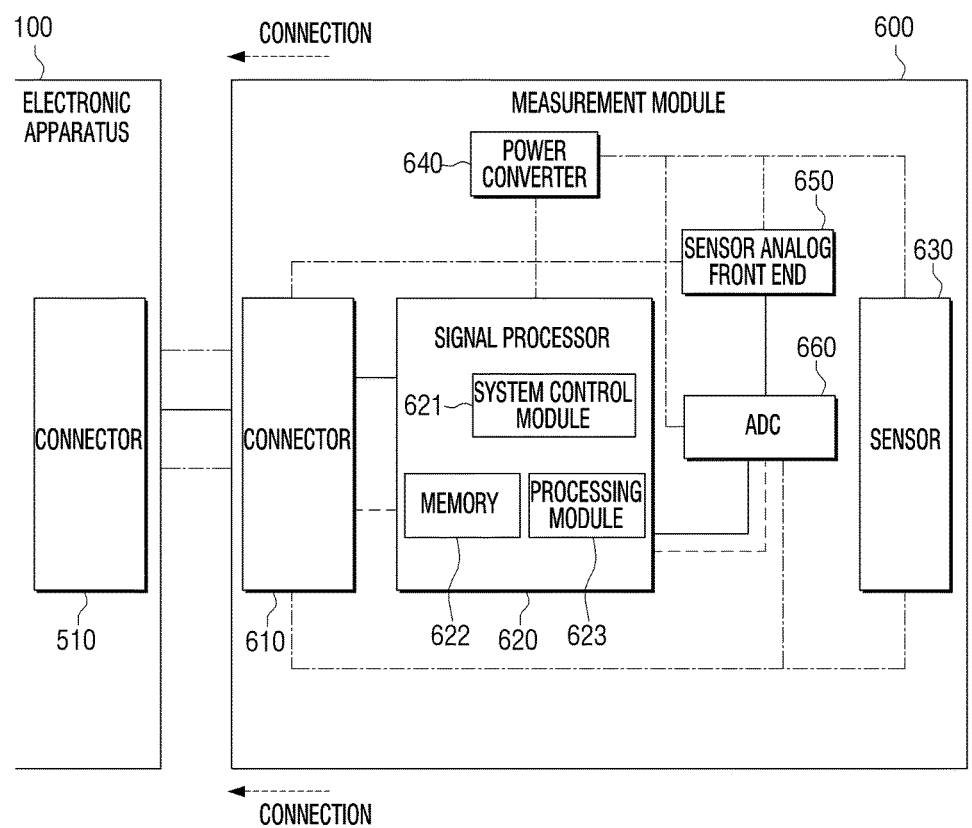
FIG. 6 is a block diagram showing a detailed configuration of a measurement module according to an exemplary embodiment.

FIG. 6 is a block diagram showing a detailed configuration of a measurement module according to an exemplary embodiment.

Referring to FIG. 6, the measurement module 600 may include a connector 610, a signal processor 620, a sensor 630, a power converter 640, a sensor analog front end 650, an analog-to-digital converter (ADC) 660.

The connector 610 may a physical connection structure to be attached to the connector 510 of the electronic apparatus 100, and may receive a driving voltage or control command from the electronic apparatus 100 via the connector 610. The connector 610 may transmit identification information of the measurement module 600 and information on a bio signal to the electronic apparatus 100.

The sensor 630 may measure a bio signal and the analog front end 650 may drive the sensor 630 and refine the bio signal measured by the sensor 630, and the ADC 660 may convert the refined bio signal into a digital signal.

The signal processor 620 may control the analog front end 650 and the ADC 660, and the analog front end 650 and the ADC 660 may be included in the signal processor 620.

The signal processor 620 may include a system control module 621 for driving the measurement module 600, a memory 622 for storing programs for driving the measurement module 600, and a processing module 623 for performing a filtering operation for additionally refining a control command received from the electronic apparatus 100 or the bio signal measured by the sensor 630.

The electronic apparatus 100 may include the power supply 560 to provide a driving voltage to the measurement module 600. However, the measurement module 600 may include the power converter 640 to convert the driving voltage provided from the electronic apparatus 100 into a driving voltage appropriate to the measurement module 600.

According to an exemplary embodiment, a system which includes an electronic apparatus which enables one of a plurality of measurement modules for measuring different types of bio signals to be selectively attached thereto and detached therefrom, and a user terminal apparatus for controlling the electronic apparatus includes: the electronic apparatus which, in response to one of the plurality of measurement modules being connected, obtains identification information of the connected measurement module and transmits the identification information to the user terminal apparatus; and the user terminal apparatus which displays a user interface screen corresponding to the connected measurement module based on the identification information of the connected measurement module, which is received from the electronic apparatus, and transmits a control command input through the user interface screen to the electronic apparatus.

The electronic apparatus may control the connected measurement module based on the received control command.

Specifically, the user terminal apparatus may receive the identification information of the measurement module connected to the electronic apparatus from the electronic apparatus via a wireless communication method, and recognize the measurement module connected to the electronic apparatus based on the received identification information. The user terminal apparatus may display a user interface screen for manipulating the connected measurement module based on the received identification information.

The user terminal apparatus may display a different user interface screen according to the measurement module connected to the electronic apparatus.

In response to information on a bio signal measured by the measurement module connected to the electronic apparatus being received, the user terminal apparatus may analyze the received information and display a result of the analyzing on the user interface screen.

For example, when the measurement module connected to the electronic apparatus is a measurement module for measuring blood glucose, in response to information on the blood glucose being received, the user terminal apparatus may analyze the information on the blood glucose and display the result of the analyzing indicating a current level of user's blood glucose on the user interface screen.

When the measurement module connected to the electronic apparatus is a measurement module for measuring a heart rate, in response to information on the heart rate being received, the user terminal apparatus may analyze the information on the heart rate and display the result of the analyzing indicating a current level of the user's heart rate on the user interface screen.

Figure 7:
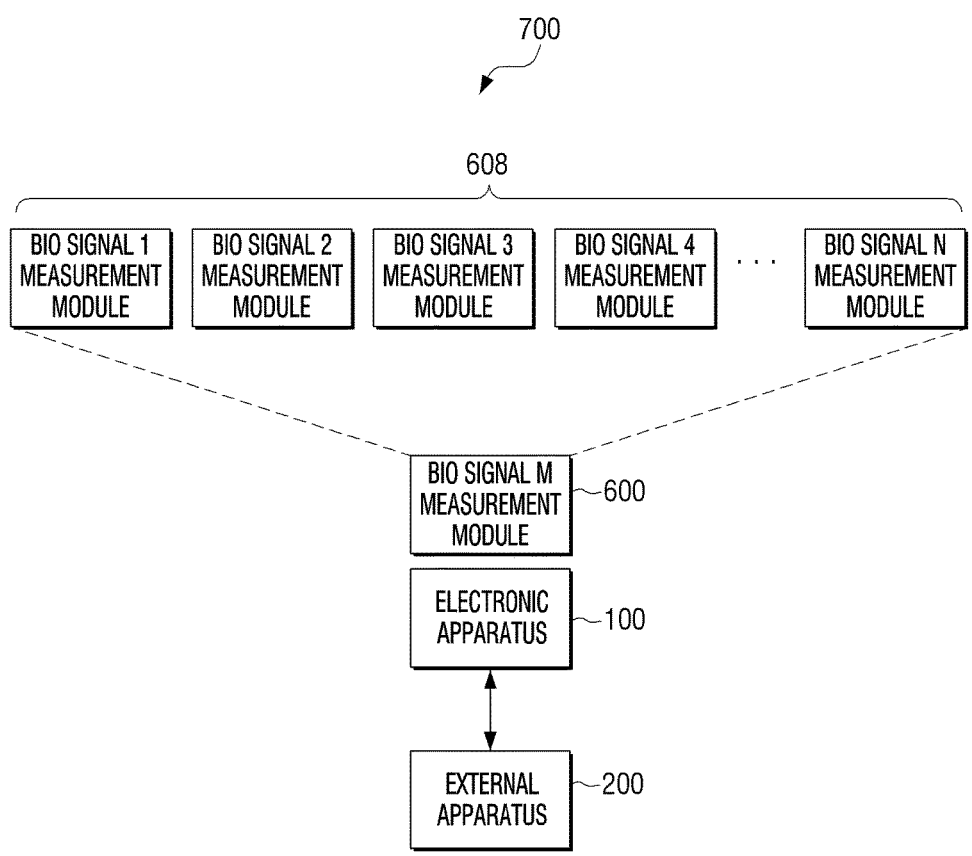
FIG. 7 is a block diagram showing a configuration of a system according to an exemplary embodiment.

FIG. 7 is a block diagram showing a configuration of a system according to an exemplary embodiment.

Referring to FIG. 7, the system 700 includes an electronic apparatus 100 to which a bio signal M measurement module 600 is attached, and an external apparatus 200. The bio signal M measurement module 600 attached to the electronic apparatus 100 may be one of a bio signal 1 measurement module, a bio signal 2 measurement module, a bio signal 3 measurement module, a bio signal 4 measurement module, . . . , and a bio signal N measurement module. The bio signal 1 measurement module, the bio signal 2 measurement module, the bio signal 3 measurement module, the bio signal 4 measurement module, . . . , and the bio signal N measurement module may measure different types of bio signals.

In response to the bio signal M measurement module 600 being attached to the electronic apparatus 100, the electronic apparatus 100 may obtain identification information of the bio signal M measurement module 600 and transmit the identification information to the external apparatus 200, and the external apparatus 200 may recognize the bio signal M measurement module 600 based on the received identification information.

The external apparatus 200 may display a user interface screen for manipulating the bio signal M measurement module 600 based on the received identification information, and may generate a control command corresponding to a user manipulation input through the user interface screen and transmit the control command to the electronic apparatus 100.

Thereafter, the electronic apparatus 100 may control the bio signal M measurement module 600 based on the control command received from the external apparatus 200.

The electronic apparatus 100 may transmit information on a bio signal measured by the bio signal M measurement module 600 to the external apparatus 200, and the external apparatus 200 may analyze information on the received bio signal and display the result of the analyzing on the user interface screen to provide it to the user.

Figure 8A:
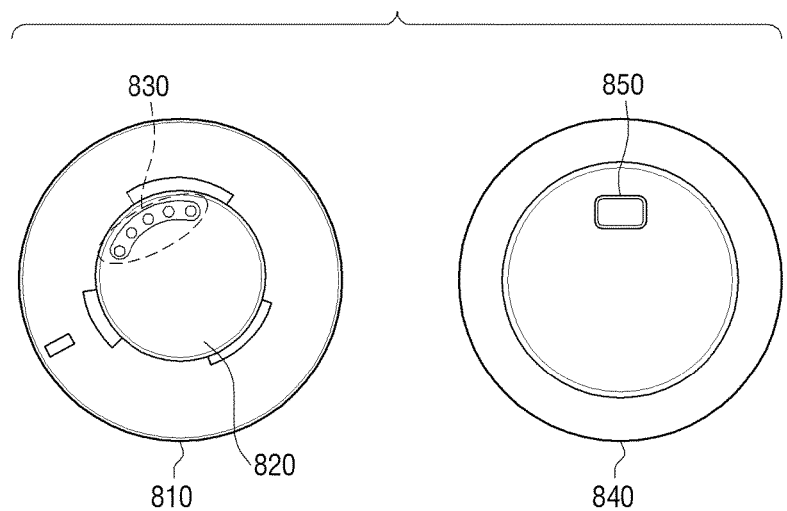
FIG. 8A is a view showing a front surface and a rear surface of an electronic apparatus according to an exemplary embodiment.

FIG. 8A is a view showing a rear surface and a front surface of the electronic apparatus according to an exemplary embodiment.

Referring to FIG. 8A, a connector 820 may be a predetermined connection structure on the rear surface 810 of the electronic apparatus 100, and a connection terminal 830 for exchanging data with a measurement module or providing a driving voltage may be provided in the connector 820.

A function key 850 for turning on or turning off the electronic apparatus 100 may be disposed on the front surface 840 of the electronic apparatus 100, and may include a touch panel which is manipulated by recognizing a touch, in addition to the function key which is manipulated by physical pressure. Although not shown in FIG. 8A, an LED lamp may be disposed on the front surface 840 of the electronic apparatus 100 to indicate the operation state of the electronic apparatus 100, an amount of power charged in the battery 140, and information on whether the battery 140 is charged.

The shape shown in FIG. 8A is merely an example and the electronic apparatus 100 may be implemented in various forms.

Figure 8B:
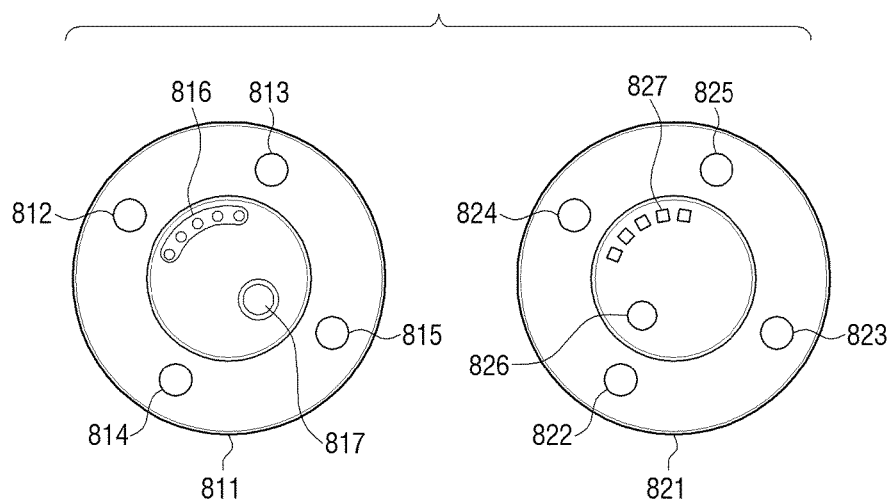
FIG. 8B is a view showing a rear surface of an electronic apparatus and a rear surface of a measurement module according to an exemplary embodiment.

FIG. 8B is a view showing a rear surface of an electronic apparatus and a rear surface of a measurement module according to an exemplary embodiment.

Referring to FIG. 8B, the electronic apparatus 100 may include magnetic substances 812, 813, 814, and 815 formed on the rear surface 811 thereof, for connecting with a measurement module. Specifically, the magnetic substances 812, 813, 814, and 815 may be divided into magnetic substances 812 and 813 having an S pole, and magnetic substances 814 and 815 having an N pole.

Likewise, the measurement module 600 may include magnetic substances 822, 823, 824, and 825 disposed on the rear surface 821 thereof, for connecting with the rear surface of the electronic apparatus 100. Specifically, the magnetic substances 822, 823, 824, and 825 may be divided into magnetic substances 822 and 823 having an S pole, and magnetic substances 824 and 825 having an N pole.

Accordingly, the magnetic substances 812 and 813 disposed on the rear surface 811 of the electronic apparatus 100 and having the S pole and the magnetic substances 824 and 825 disposed on the rear surface 821 of the measurement module and having the N pole may attract each other and thereby may be connected with each other, and the magnetic substances 814 and 815 disposed on the rear surface 811 of the electronic apparatus 100 and having the N pole and the magnetic substances 822 and 823 having the S pole may attract each other and thereby may be connected with each other. Accordingly, the electronic apparatus 100 and the measurement module may be connected with each other.

In response to the electronic apparatus 100 and the measurement module being connected with each other and the user rotating at least one of the electronic apparatus 100 and the measurement module by a predetermined angle, the magnetic substances 812 and 813 disposed on the rear surface 811 of the electronic apparatus 100 and having the S pole and the magnetic substances 822 and 823 disposed on the rear surface 821 of the measurement module and having the S pole may repel each other, and the substances 814 and 815 disposed on the rear surface 811 of the electronic apparatus 100 and having the N pole and the magnetic substances 824 and 825 disposed on the rear surface 821 of the measurement module and having the N pole may repel each other, such that the electronic apparatus 100 and the measurement module can be easily separated from each other.

The electronic apparatus 100 may include a groove structure 817 formed on the rear surface 811 thereof, and the measurement module may include a protrusion 826 formed on the rear surface 821 thereof to be inserted into the groove structure 817 included in the rear surface 811 of the electronic apparatus 100. Accordingly, when the groove structure 817 included in the rear surface 811 of the electronic apparatus 100 and the protrusion 826 included in the rear surface 821 of the measurement module are connected with each other, the electronic apparatus 100 and the measurement module can be securely connected with each other by the magnetic force without being misaligned from each other.

The electronic apparatus 100 may include a connection terminal 816 formed on the rear surface 811 thereof to exchange data with the measurement module or provide a driving voltage, and the measurement module may include a connection terminal 827 formed on the rear surface 821 thereof to connect with the connection terminal 816 included in the rear surface 811 of the electronic apparatus 100. By means of these connection terminals 816 and 827, the electronic apparatus 100 and the measurement module may exchange data with each other or may provide and receive a driving voltage. The data may include data regarding a bio signal, a driving signal for starting measuring a bio signal, and a control signal for stopping measuring a bio signal.

In FIG. 8B, four magnetic substances are included in each of the rear surface 811 of the electronic apparatus 100 and the rear surface 821 of the measurement module as an example. However, the number of magnetic substances is not limiting.

Figure 9:
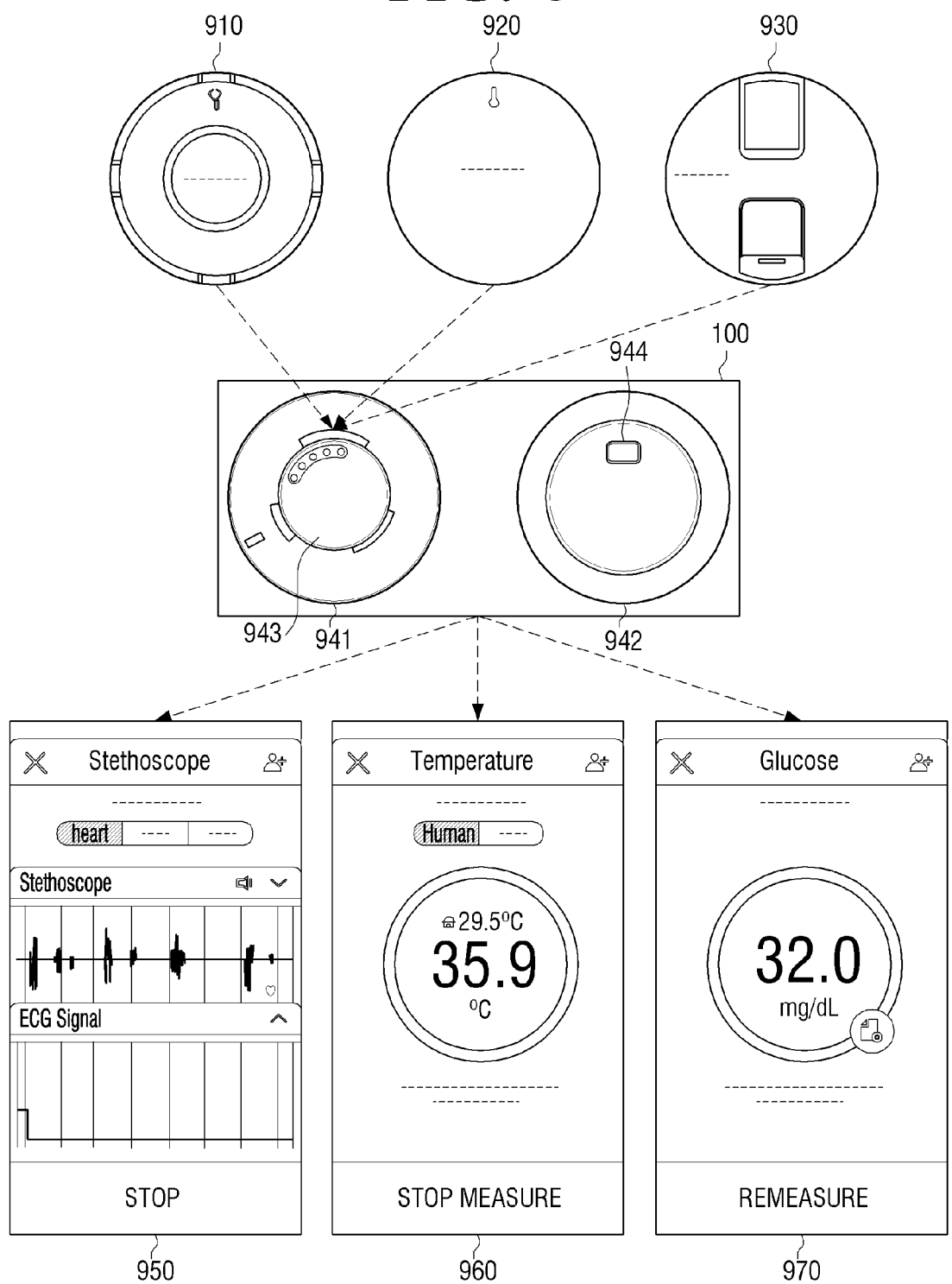
FIG. 9 is a view showing a detailed configuration of a system according to an exemplary embodiment.

FIG. 9 is a view showing a detailed configuration of a system according to an exemplary embodiment.

Referring to FIG. 9, a plurality of measurement modules 608 for measuring different types of bio signals may include at least one among a measurement module 910 for doing an ECG, a measurement module 920 for measuring body temperature, and a measurement module 930 for measuring blood glucose, and one of them may be selectively attached to a connector 943 disposed on a rear surface 941 of an electronic apparatus 100.

In response to a function key 944 disposed on a front surface 942 of the electronic apparatus 100 being manipulated by the user, the electronic apparatus 100 may be turned on and may transmit identification information of a measurement module attached to the connector 943 to an external apparatus.

Thereafter, the external apparatus may recognize the measurement module attached to the electronic apparatus 100 based on the received identification information, and display a user interface screen 950, 960, or 970 corresponding to the recognized measurement module.

The first user interface screen 950 may correspond to the measurement module 910 for doing the ECG, the second user interface screen 960 may correspond to the measurement module 920 for measuring the body temperature, and the third user interface 970 may correspond to the measurement module 930 for measuring the blood glucose.

In response to information on a bio signal measured by the measurement module attached to the electronic apparatus 100 being received, the external apparatus may analyze the information on the bio signal and display the result of the analyzing on the user interface screen 950, 960, or 970. In FIG. 9, the first user interface screen 950 may display a result of analyzing a heart rate, the second user interface screen 960 may display a result of analyzing body temperature, and the third user interface screen 970 may display a result of analyzing blood glucose.

The external apparatus 200 may communicate with the electronic apparatus 100 in various ways to receive the information on the bio signal. This will be described below with reference to FIGS. 10 and 11.

Figure 10:
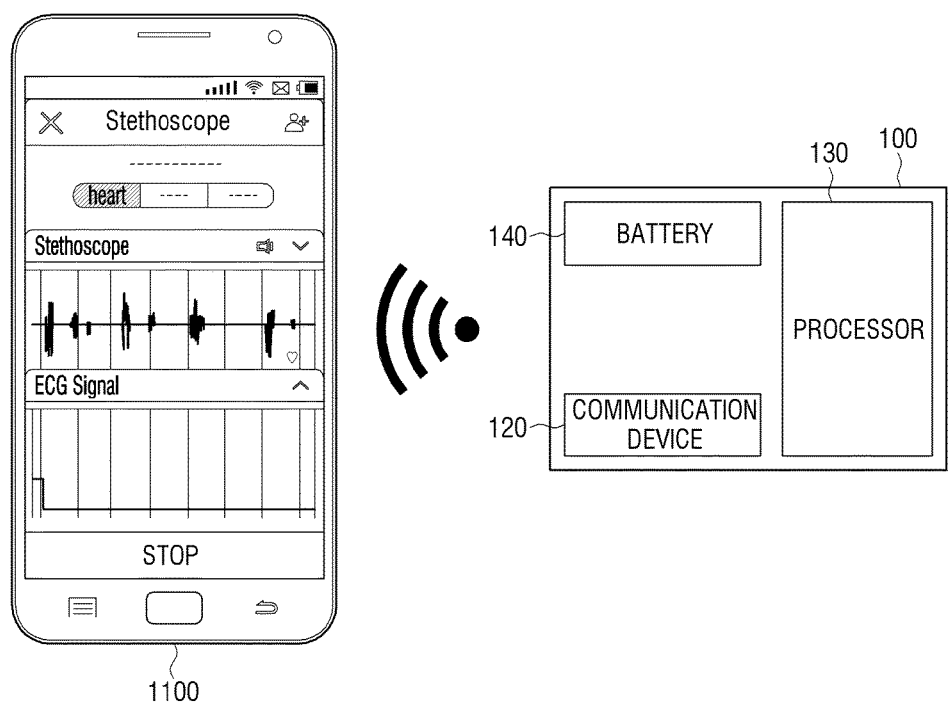
FIGS. 10 and 11 are views showing a communication method between an external apparatus and an electronic apparatus according to an exemplary embodiment.
Figure 11:
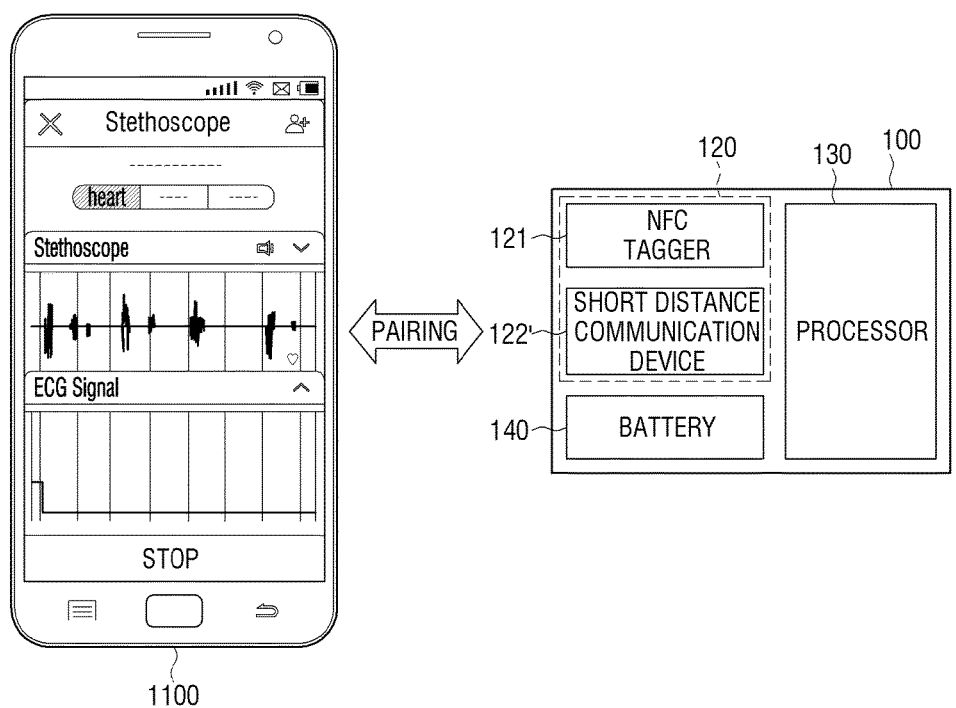

FIGS. 10 and 11 are views to illustrate a communication method between an external apparatus and an electronic apparatus according to an exemplary embodiment.

Referring to FIG. 10, the external apparatus 200 includes a smart phone 1100, and the smart phone 1100 may communicate with the electronic apparatus 100. Specifically, the smart phone 1100 may communicate by connecting a communication session with the communication device 120 of the electronic apparatus 100, and may receive information on a bio signal from the electronic apparatus 100, analyze the information on the bio signal, and generate a result of the diagnosing, and may display the result of the diagnosing through the user interface screen 950, 960, or 970 shown in FIG. 9.

In particular, in response to the identification number of a measurement module connected to the electronic apparatus 100 being received, the smart phone 1100 may identify what type of bio signal the measurement module connected to the electronic apparatus 100 measures based on the identification number of the measurement module, and may select and execute a software program or application for driving the identified measurement module, and may display a user interface screen corresponding to the identified measurement module.

The smart phone 1100 may communicate with the electronic apparatus 100 and transmit a control command for controlling the measurement module to the electronic apparatus 100. Specifically, the smart phone 1100 may transmit a control command for starting measuring a bio signal to the electronic apparatus 100 or may transmit a control command for stopping measuring the bio signal to the electronic apparatus 100.

For example, when the measurement module connected to the electronic apparatus 100 is a heart rate measurement module, the smart phone 1100 may transmit a control command for starting measuring a hear rate to the electronic apparatus 100, and, in response to a user manipulation for stopping measuring the heart rate being input or a predetermined time elapsing, the smart phone 1100 may transmit a control command for stopping measuring the heart rate to the electronic apparatus 100.

Referring to FIG. 11, the communication device 120 of the electronic apparatus 100 may include the NFC tagger 121 and a short distance communication device 122'.

Specifically, in response to the smart phone 1100 and the electronic apparatus 100 being adjacent to each other within a predetermined range, the electronic apparatus 100 may exchange information for WiFi or Bluetooth communication pairing with the smart phone 1100 with the smart phone 1100 via the NFC tagger 121, and, in response to the WiFi or Bluetooth communication pairing being completed, the electronic apparatus 100 may transmit identification information of the measurement module connected to the electronic apparatus 100 to the smart phone 1100 via WiFi or Bluetooth communication. The short distance communication device 122' may perform WiFi or Bluetooth communication.

The smart phone 1100 may automatically display a user interface screen corresponding to the measurement module currently connected to the electronic apparatus 100 based on the identification information of the measurement module connected to the electronic apparatus 100, which is received via WiFi or Bluetooth communication.

In response to a user manipulation for selecting an item for diagnosing being input, the external apparatus may provide guide information on the measurement module which is required for the selected diagnosis item. This will be described below with reference to FIGS. 12A to 12F.

FIGS. 12A to 12F are views showing an external apparatus 1200 which displays guide information for a user according to an exemplary embodiment. The external apparatus 1200 corresponds to the external apparatus 200 described above.

Figure 12A:
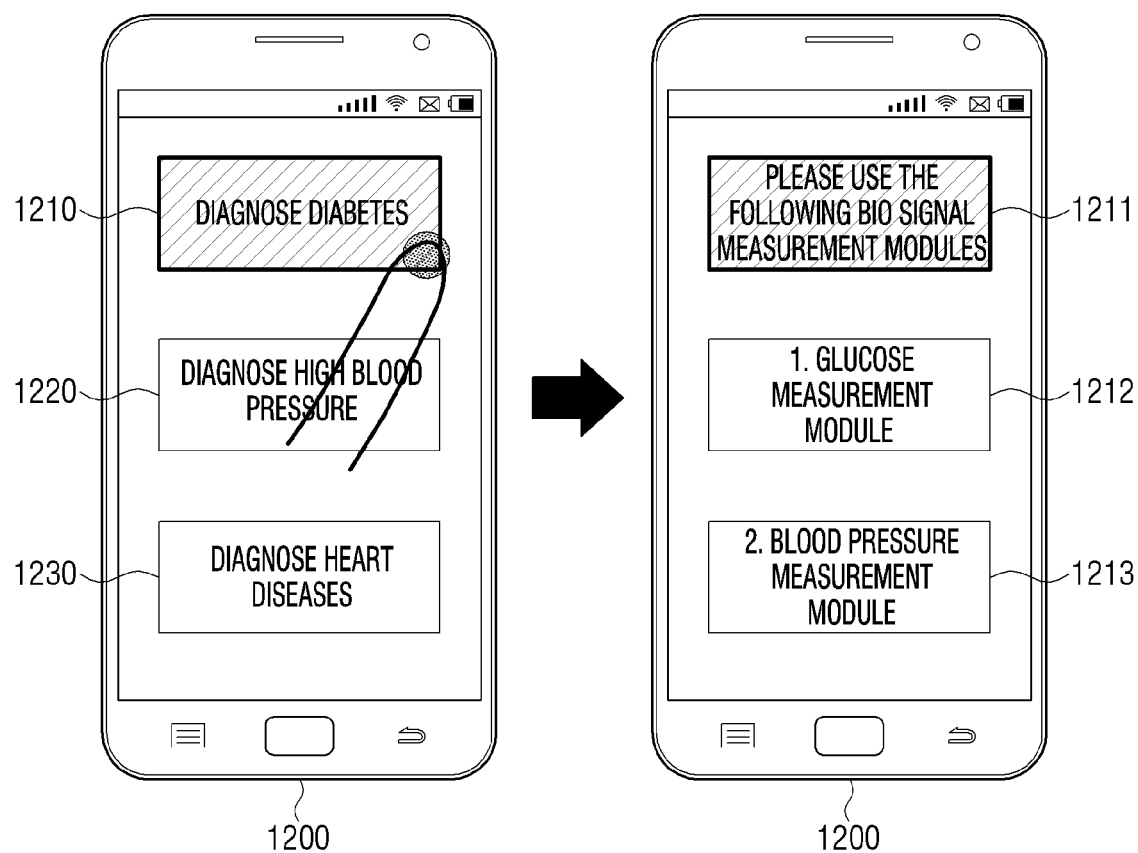
FIGS. 12A, 12B, 12C, 12D, 12E, and 12F are views showing guide information which is displayed for a user by an external apparatus according to an exemplary embodiment.

Referring to FIG. 12A, the external apparatus 1200 may display a user interface screen including a plurality of items 1210, 1220, and 1230 for diagnosing.

Specifically, the plurality of items 1210, 1220, and 1230 for diagnosing may include a diabetes diagnosis item 1210, a high blood pressure diagnosis item 1220, a heart disease diagnosis item 1230, or the like, and each of the items may be expressed by an icon and/or a graphical user interface (GUI).

A diagnosis item which is selected by a user touch from the plurality of items 1210, 1220, and 1230 may be highlighted, may be displayed in different color from that of the other diagnosis items, or may be a GUI interposed on the text or on an image, e.g., a visually distinguishable border, to indicate that the item is selected.

The external apparatus 1200 may display guide information informing of which measurement module is to measure a bio signal related to the selected diagnosis item.

For example, in response to the diabetes diagnosis item 1210 being selected by the user touch on the user interface screen, the external apparatus 1200 may display guide information informing of a measurement module for measuring a bio signal for diagnosing diabetes. Specifically, the external apparatus 1200 may display guide information 1211 informing of the measurement module or modules needed for a certain diagnosis, that is, a blood glucose measurement module 1212 and a blood pressure measurement module 1213. The guide information 1211 may be the text "Please use the following bio signal measurement modules."

When a plurality of bio signals are needed to diagnose diabetes, the external apparatus 1200 may display priority order of attaching and/or connecting the measurement modules to inform of an order of measuring respective bio signals.

That is, the external apparatus 1200 may display "1. Blood glucose measurement module 1212" and "2. Blood pressure measurement module 1213," providing guide information on the order of measurement indicating that the user should start measuring by connecting the blood glucose measurement module to the electronic apparatus 100, first, and then continue measuring by connecting the blood pressure measurement module to the electronic apparatus 100.

Accordingly, the user may easily understand which the measurement modules are needed for a certain diagnosis according to the guide information provided by the external apparatus 1200, and may connect the measurement modules needed for a certain diagnosis to the electronic apparatus 100 in the appropriate order.

In FIG. 12A, the external apparatus 1200 displays the measurement modules needed for a certain diagnosis 1212 and 1213 using texts, but may display images indicating the respective measurement modules with the texts.

Specifically, the external apparatus 1200 may display the images of the measurement modules 1212 and 1213 with the texts.

Figure 12B:
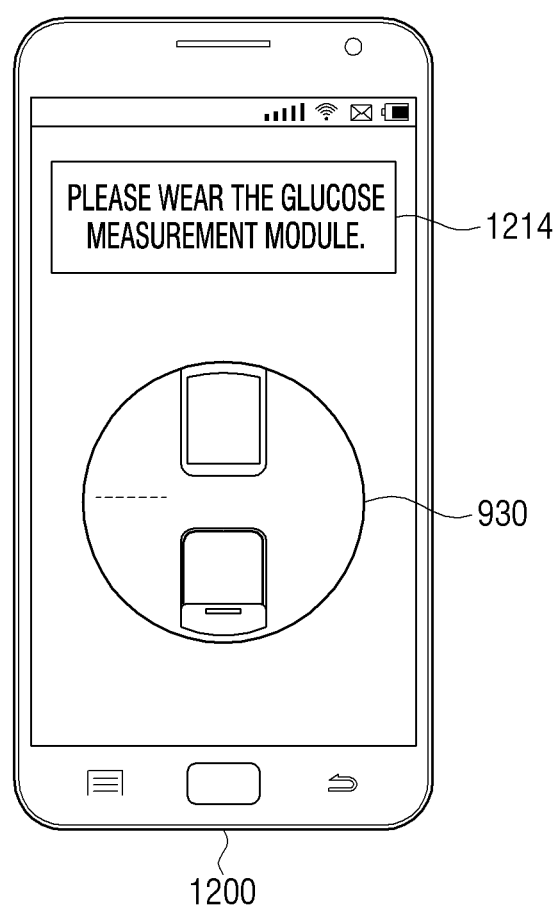

For example, referring to FIG. 12B, the external apparatus 1200 may display an image showing the appearance of the measurement module 930 for measuring blood glucose, shown in FIG. 9, with a text "Please mount the blood glucose measurement module" 1214.

Figure 12C:
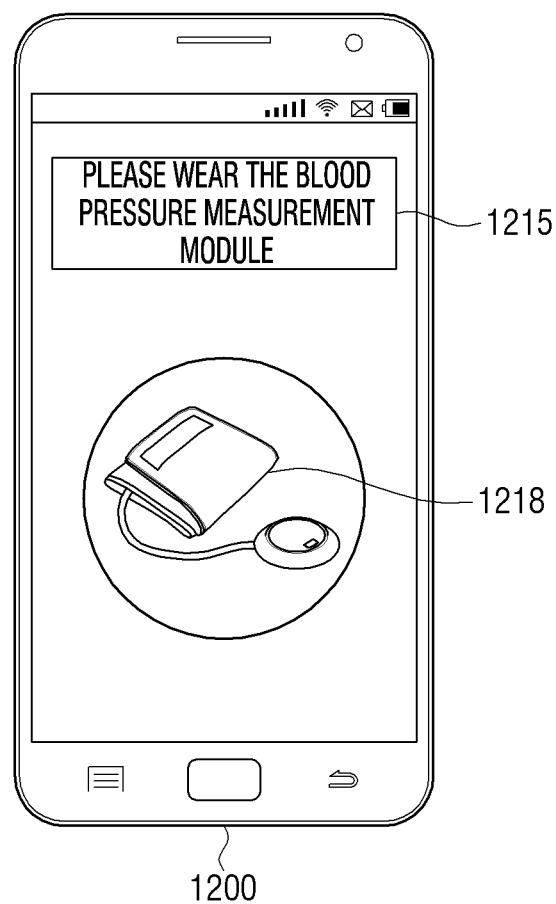

Referring to FIG. 12C, the external apparatus 1200 may display an image showing the appearance of the blood pressure measurement module 1218 with a text "Please mount the blood pressure measurement module" 1215.

In response to the user touching the diabetes diagnosis item 1210 on the screen of the external apparatus 1200 as shown in FIG. 12A, the external apparatus 1200 may display the guide information with the text 1211 informing the user that the blood glucose measurement module 1212 and the blood pressure measurement module 1213 are needed to diagnose diabetes, and also may display priority order as numbers indicating the order of measurement. In response to the user touching "1. Blood glucose measurement module 1212," the external apparatus 1200 may display the image showing the appearance of the measurement module 930 for measuring blood glucose, as shown in FIG. 12B, and thereby guide the user to connect the measurement module 930 for measuring blood glucose to the electronic apparatus 100.

In response to the user touching "2. Blood pressure measurement module 1213," the external apparatus 1200 may display the image showing the appearance of the blood pressure measurement module 1218 as shown in FIG. 12C, and thereby guide the user to connect the blood pressure measurement module 1218 to the electronic apparatus 100.

The external apparatus 1200 may provide guide information informing the user how to use or wear the measurement modules needed for a certain diagnosis, in addition to the guide information on the measurement modules for the diagnosis item selected by the user manipulation.

Figure 12D:
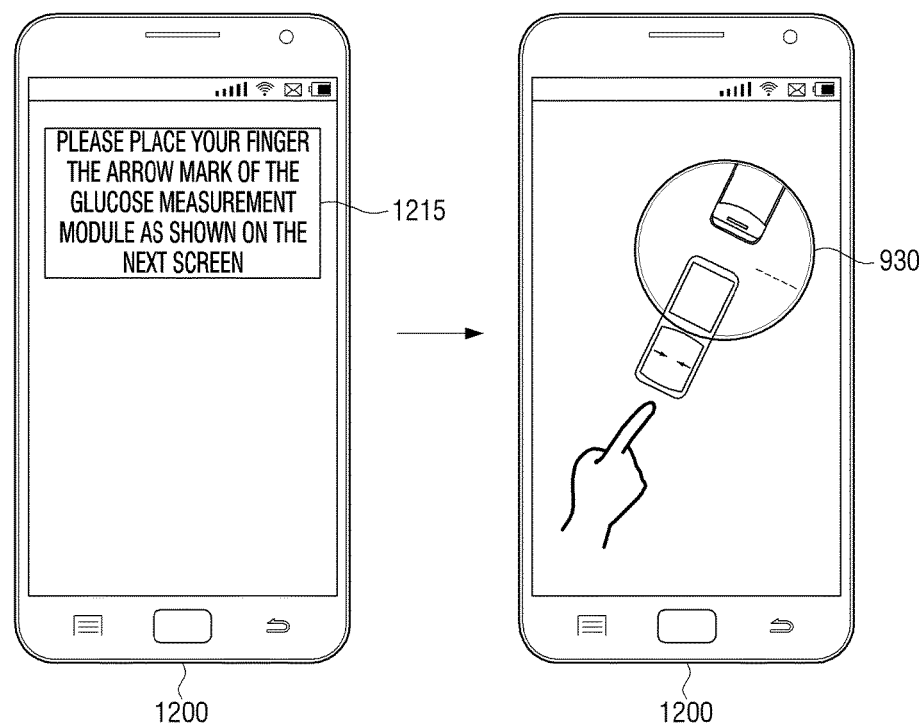

Referring to FIG. 12D, in response to the user connecting the measurement module 930 for measuring blood glucose to the electronic apparatus 100, the external apparatus 1200 may display a text 1216 "Please place your finger the arrow mark of the blood glucose measurement module as shown on the next screen," and may display an image showing a user's operation of placing user's finger on the arrow mark of the measurement module 930 for measuring blood glucose.

Figure 12E:
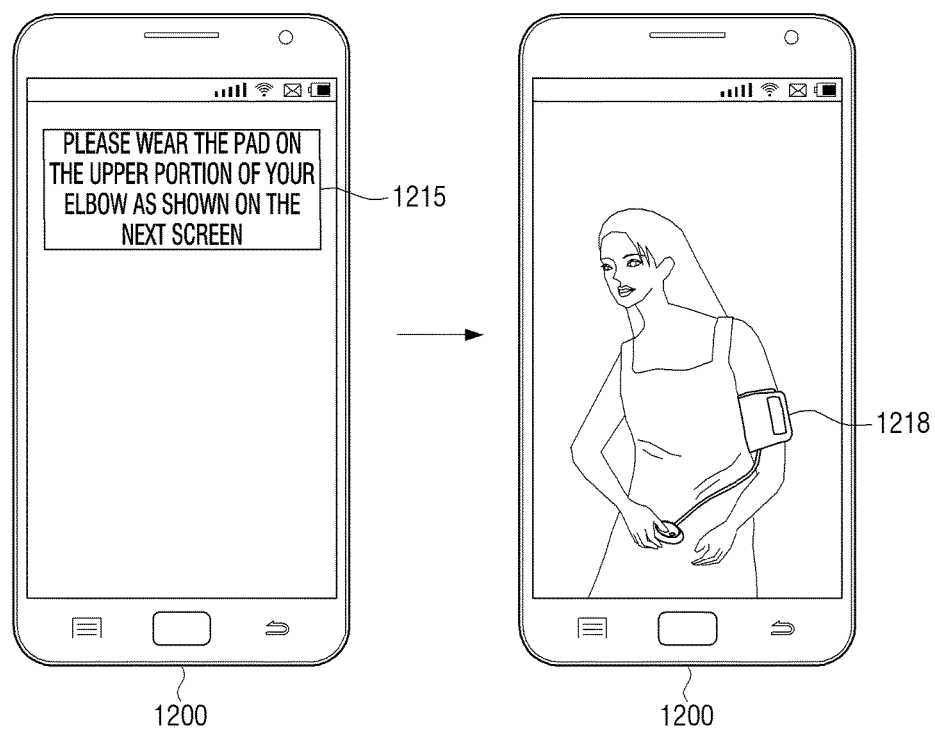

Referring to FIG. 12E, in response to the user connecting the blood pressure measurement module 1218 to the electronic apparatus 100, the external apparatus 1200 may display a text 1217 "Please wear the pad on the upper portion of your elbow as shown on the next screen," and may display an image showing a user's operation of wearing the blood pressure measurement module 1218 on the arm.

Accordingly, the user may recognize which measurement module the user should select regarding the diagnosis item selected by the user, and also, may get to know how to use or wear the selected measurement module.

In the above-described examples, only the blood glucose measurement module and the blood pressure measurement module related to the diagnosis of diabetes have been described. However, the external apparatus 1200 may provide guide information on the measurement modules related to various health diagnosis items in addition to diagnosis of high blood pressure and diagnosis of a heart disease, and using methods of the measurement modules through texts or images.

In the above-described example, the external apparatus 1200 may provide the guide information on the measurement modules needed for a certain diagnosis and the using methods of the measurement modules through texts or images. However, the external apparatus 1200 may provide the guide information to the user by reproducing a video related to the measurement modules needed for a certain diagnosis and the using methods of the measurement modules or outputting a related voice.

On the other hand, in response to the measurement module currently connected to the electronic apparatus 100 not being the measurement module needed for the item for diagnosing, the external apparatus 1200 may display guide information indicating that the measurement module currently connected to the electronic apparatus 100 is not the measurement module needed for the diagnosis item selected by the user.

Figure 12F:
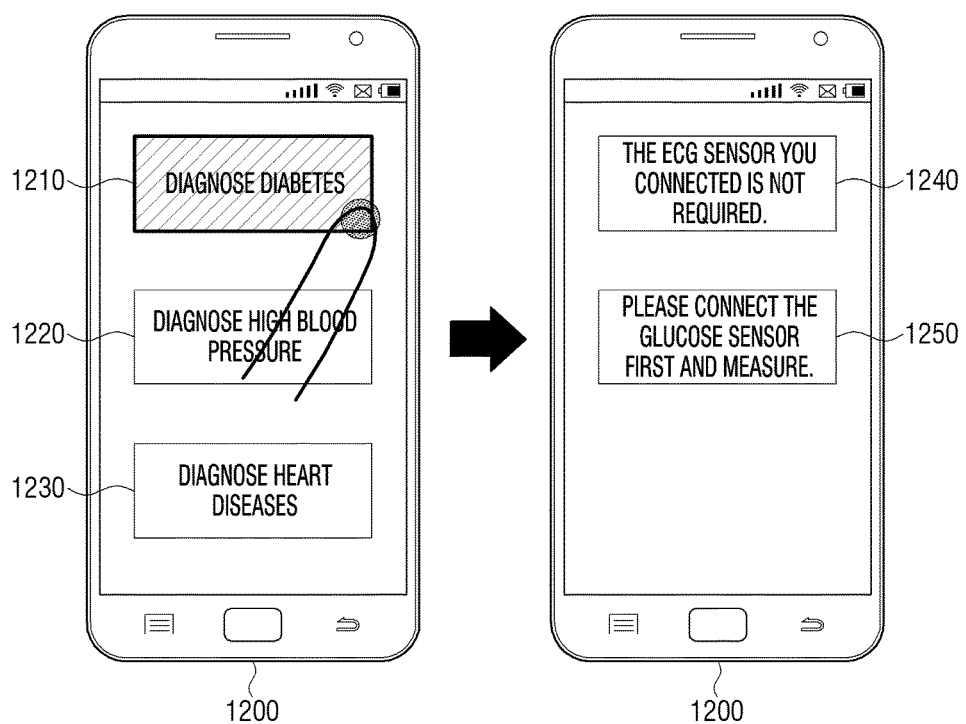

For example, referring to FIG. 12F, on the assumption that the measurement module currently connected to the electronic apparatus 100 is an ECG measurement module, in response to the diabetes diagnosis item 1210 being selected by a user touch on the user interface screen, the external apparatus 1200 may display guide information 1240 "The ECG sensor you connected is not required," indicating that the ECG measurement module connected to the electronic apparatus 100 is not needed in relation to the currently selected diabetes diagnosis item 1210.

Along with this, the external apparatus 1200 may display a message 1520 "Please connect the blood glucose measurement module, first, and measure" to inform of the measurement module for the selected diabetes diagnosis item 1210.

Accordingly, the user may disconnect the ECG measurement module from the electronic apparatus 100 in order to diagnose diabetes, and may start measuring by following the provided instructions and connecting the blood glucose measurement module to the electronic apparatus 100.

In response to the user disconnecting the ECG measurement module from the electronic apparatus 100 and connecting the blood glucose measurement module to the electronic apparatus 100, the external apparatus 1200 may output a message indicating that the measurement module needed for a certain diagnosis is currently connected to the electronic apparatus 100.

In addition, in response to the measurement module currently connected to the electronic apparatus 100 not being the measurement module for the item for diagnosing, the external apparatus 1200 may inform the user that the measurement module currently connected to the electronic apparatus 100 is not the measurement module for the diagnosis item selected by the user through a message, and also, the electronic apparatus 100 may inform the user directly through an LED or a vibration.

For example, the electronic apparatus 100 may include an LED, an acceleration sensor, and a vibration motor. The electronic apparatus 100 may include an LED for indicating information on the operation state of the electronic apparatus 100, the amount of power charged in the battery, and whether the battery is charged. The electronic apparatus 100 may indicate that a different measurement module is connected to the electronic apparatus 100 through the same LED as described in FIG. 4, or may indicate that a different measurement module is connected to the electronic apparatus 100 through a separate LED.

Specifically, the external apparatus 1200 may receive, from the electronic apparatus 100, the identification information of the measurement module connected to the electronic apparatus 100, and may determine whether the measurement module currently connected to the electronic apparatus 100 is the same as the measurement module provided through the guide information provided by the external apparatus 1200, based on the received identification information of the measurement module.

As a result, in response to the measurement module currently connected to the electronic apparatus 100 being different from the measurement module provided through the guide information provided by the external apparatus 1200, the external apparatus 1200 may transmit, to the electronic apparatus 100, a warning output control signal for informing that a different measurement module is connected to the electronic apparatus 100, and the electronic apparatus 100 which has received the warning output control signal may transmit a warming message to the user using LED lamp color or vibration through the LED or the vibration motor provided in the electronic apparatus 100.

The external apparatus 1200 may transmit the warming output control signal to the electronic apparatus 100 in phases, and accordingly, the electronic apparatus 100 may transmit the warming message to the user in phases.

For example, the user may select the diabetes diagnosis item and thus the external apparatus 1200 may transmit guide information on the blood glucose measurement module and the blood pressure measurement module related to the diagnosis of diabetes to the electronic apparatus 100. In this state, in response to the user connecting a body temperature measurement module to the electronic apparatus 100, the external apparatus 1200 may determine that a different measurement module having nothing to do with the diagnosis of diabetes is connected to the electronic apparatus 100 based on received identification information of the body temperature measurement module, and may transmit, to the electronic apparatus 100, a first warning output control signal for controlling the LED of the electronic apparatus 100 to emit light in predetermined color. The electronic apparatus 100 may control the LED provided therein to emit light in the predetermined color based on the received first warning output control signal. For example, in response to a different measurement module being connected to the electronic apparatus 100, the electronic apparatus 100 may control the LED emit light in red color, and, in response to a correct measurement module being connected to the electronic apparatus 100, the electronic apparatus 100 may control the LED to emit light in blue color.

In response to the user moving the electronic apparatus 100 to start measuring using the body temperature measurement module connected to the electronic apparatus 100, without recognizing that the LED emits a warning light in the certain color, the electronic apparatus 100 may determine the movement of the electronic apparatus 100 through the acceleration sensor provided therein, and transmit information on the acceleration sensor value to the external apparatus 1200.

The external apparatus 1200 may determine that the user uses the different measurement module having nothing to do with the diagnosis of diabetes based on the information on the acceleration sensor value, and transmit, to the electronic apparatus 100, a second warning output control signal for controlling the electronic apparatus 100 to output a vibration. The electronic apparatus 100 may control to output the vibration through the vibration motor provided therein based on the received second warning output control signal.

As described above, the electronic apparatus 100 provides the warning messages to the user in phases, such that the user can be continuously guided to select an exact measurement module.

FIGS. 13A to 13K are views to illustrate a receiving box for receiving an electronic apparatus, a plurality of measurement modules, and an external apparatus according to an exemplary embodiment.

Figure 13A:
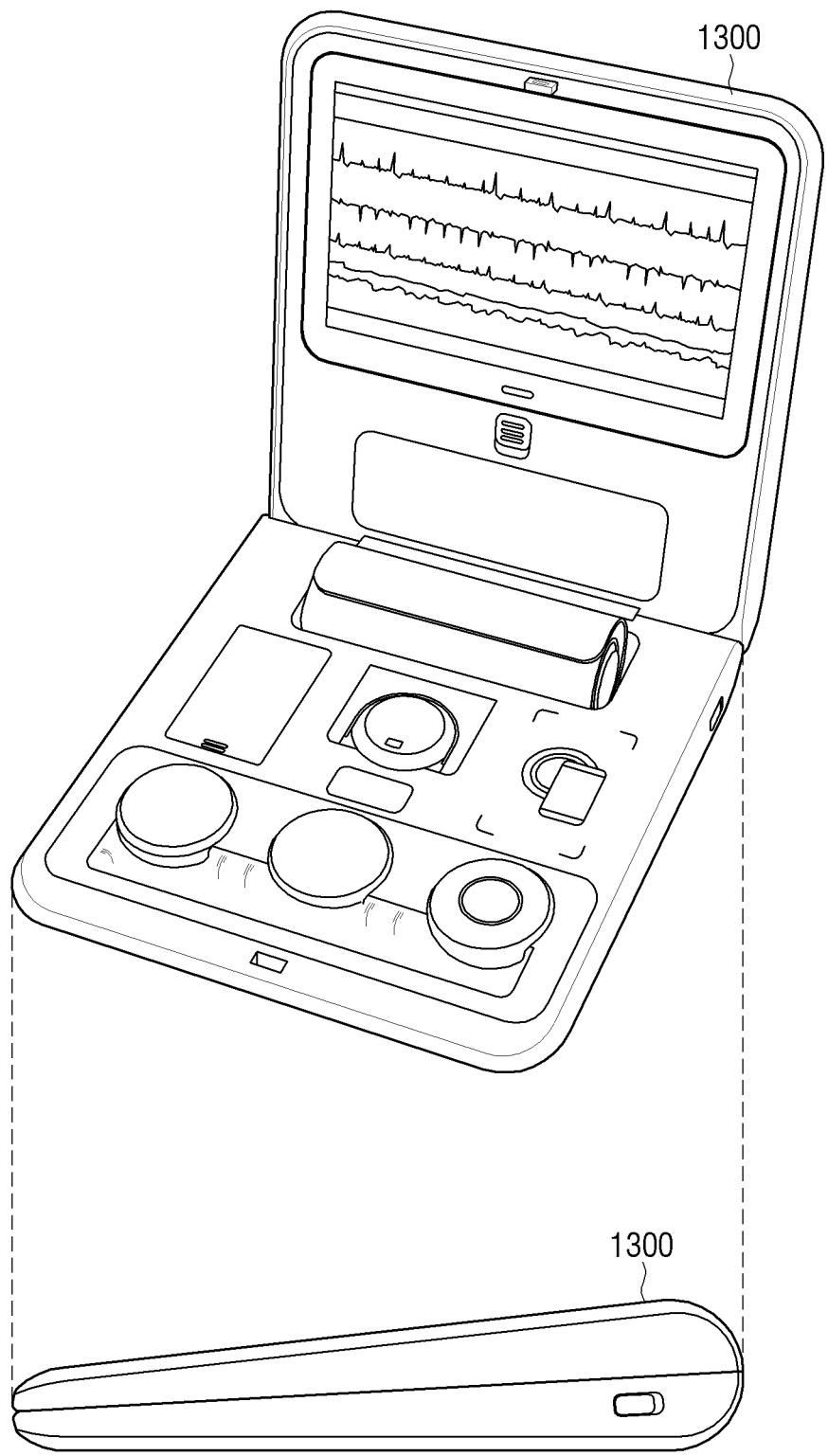
FIGS. 13A, 13B, 13C, 13D, 13E, 13F, 13G, 13H, 13I, 13J, and 13K are views illustrating a receiving box for receiving an electronic apparatus, a plurality of measurement modules, and an external apparatus according to an exemplary embodiment.

Referring to FIG. 13A, the receiving box 1300 may receive the plurality of measurement modules, the electronic apparatus, and the external apparatus, and may be implemented by using a hinge structure similar to a notebook PC, such that the receiving box 1300 can be used by opening a cover of an upper end. The receiving box 1300 may receive the external apparatus such as a tablet in an inner space formed on the upper end thereof, and may receive the various measurement modules and the electronic apparatus in inner spaces formed on the lower end thereof.

The receiving box 1300 may be closed by bringing the cover of the upper end into close contact with the lower end with the plurality of measurement modules, the electronic apparatus, and the external apparatus being received therein, such that thickness of the receiving box 1300 can be reduced and thus portability and convenience can be enhanced.

Figure 13B:
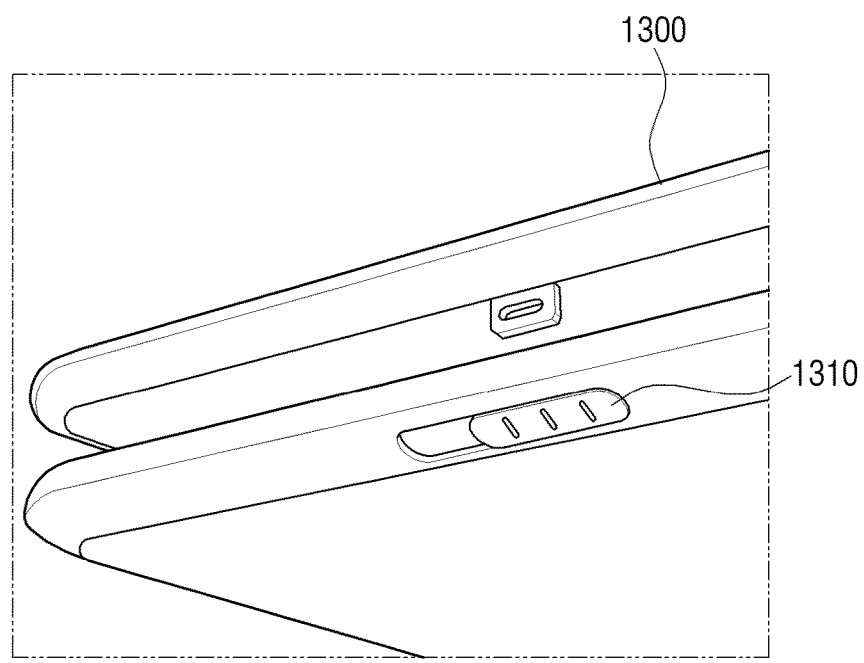

Referring to FIG. 13B, a locking device 1310 may be disposed on one area of the lower end of the receiving box 1300, and, in response to the cover of the upper end being engaged with one area of the lower end, a hook part included in the cover of the upper end is locked into one area of the lower end by the locking device 1300, and the user may unlock by sliding the locking device 1310 in one direction and may raise up the cover of the upper end.

In FIG. 13B, physical structures, e.g., the hook part included in the cover of the upper end and the locking device 1310 included in one area of the lower end are described as an example, but the locking device 1310 may include a structure using a magnetic substance or a structure using a fingerprint recognition device, in addition to the physical structure.

Figure 13C:
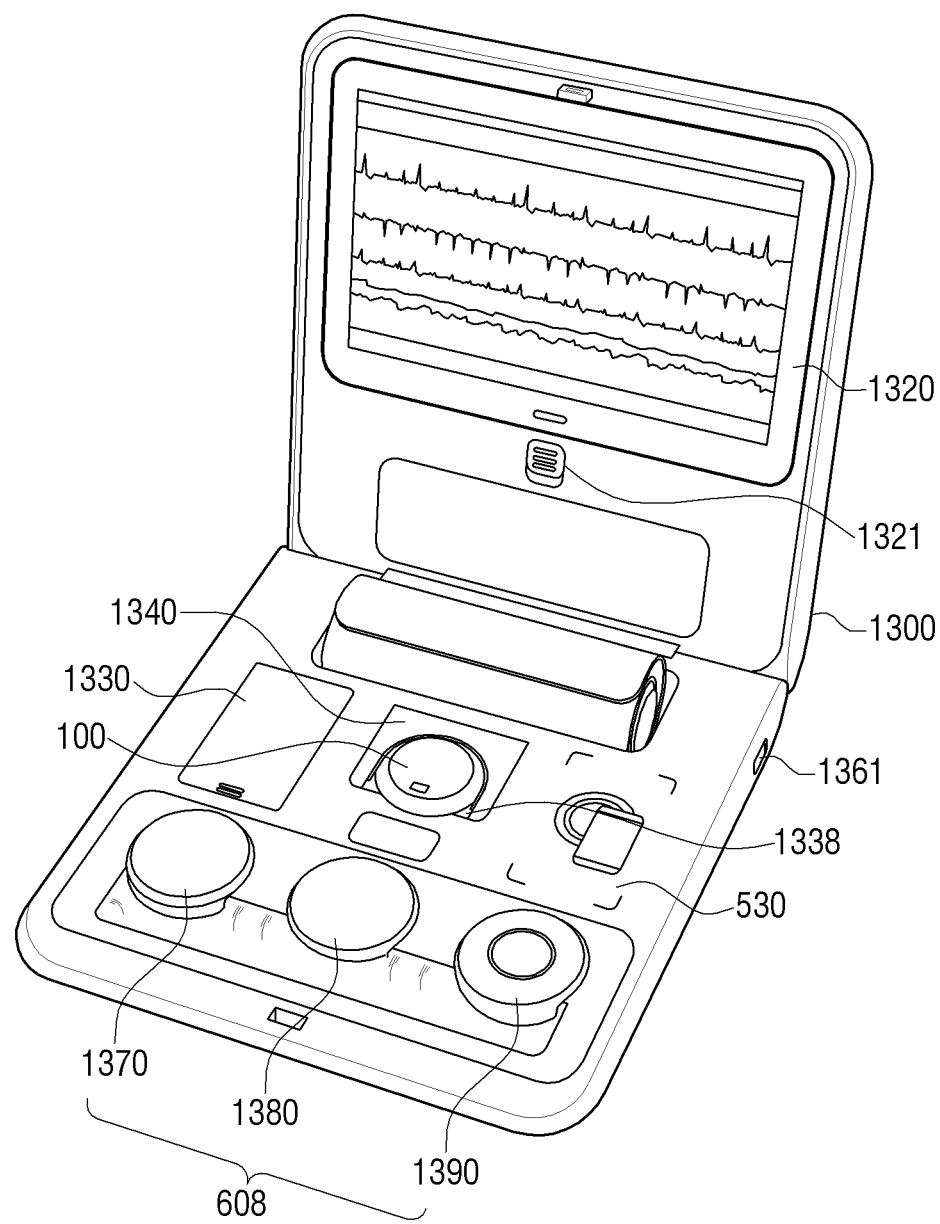

Specifically, referring to FIG. 13C, the external apparatus 200 may include a tablet PC 1320. The tablet PC 1320 may be received inside the cover of the upper end, and a button 1321 may be disposed under the receiving space of the tablet PC 1320, and may include an interface for fixing the tablet PC 1320 and transmitting data between the tablet PC 1320 and the receiving box 1300.

A plurality of measurement modules 608 including measurement modules 1370, 1380, and 1390 may be received in the lower end of the receiving box 1300, and a space 1338 for separately receiving an electronic apparatus 100 may be disposed on the lower end of the receiving box 1300. The space 1338 for separately receiving the electronic apparatus 100 may include a circuit for charging the electronic apparatus 100, e.g., a charger 1340. Accordingly, the electronic apparatus 100 may be charged when the electronic apparatus 100 is received in the charger 1340.

A separate receiving space 1330 may be disposed on the lower end of the receiving box 1300, and may contain user's necessary articles.

An NFC tagger 530 may be disposed on the lower end of the receiving box 1300. The electronic apparatus 100 may perform tagging with the NFC tagger 530 included in the lower end of the receiving box 1300, and may transmit information for short distance communication pairing with the tablet PC 1320 disposed on the upper end of the receiving box 1300, such as Bluetooth communication, to the tablet PC 1320. In response to the short distance communication pairing being completed between the tablet PC 1320 and the electronic apparatus 100, identification information of a measurement module currently connected to the electronic apparatus 100 may be transmitted to the tablet PC 1320.

In addition, various input and output ports such as a USB port 1361, an HDMI port, or the like may be disposed on the lower end of the receiving box 1300, and the receiving box 1300 may be charged via the USB port 1361 and may transmit and store data in an external memory device connected via the USB port 1361. The receiving box 1300 may transmit a result of diagnosing to a display apparatus such as a TV via an output port such as an HDMI port to display the result, and may output the result via an output port such as a printer port as a document.

Figure 13D:
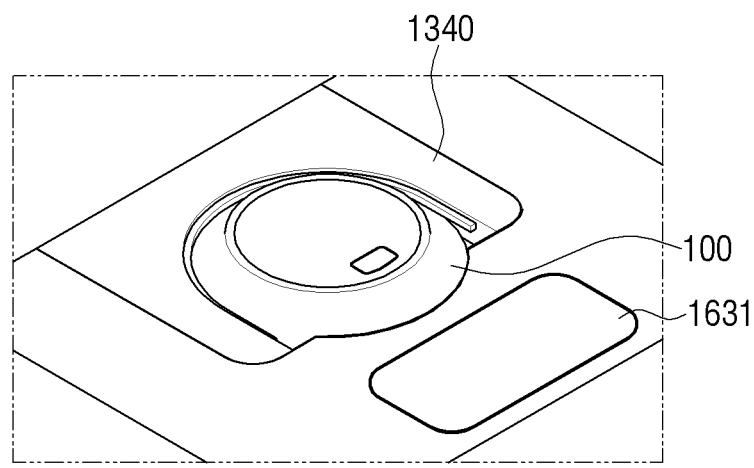
Figure 13E:
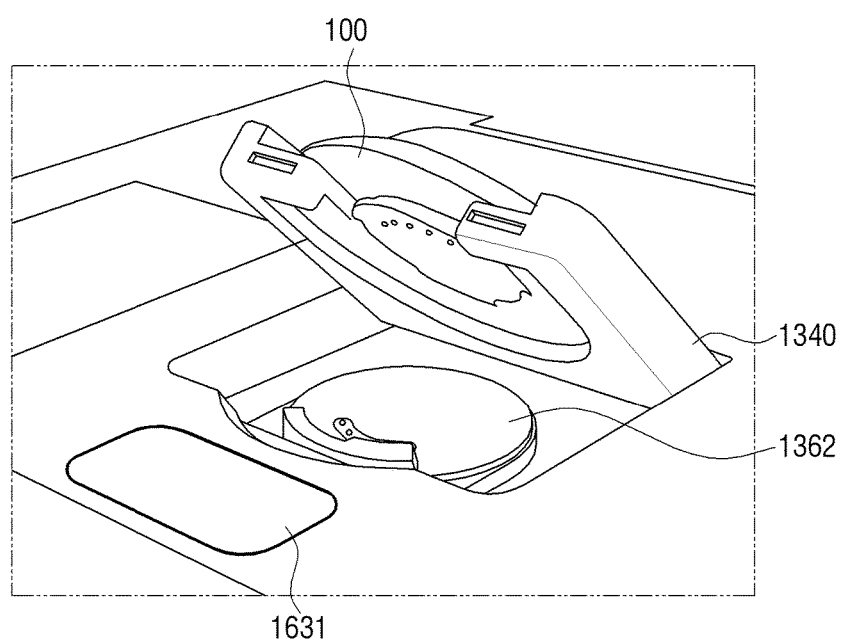

FIGS. 13D and 13E are views illustrating the charger 1340 which receives the electronic apparatus 100 in detail, and referring to FIG. 13D, a physical button 1631 may be disposed close to the charger 1340, in which the electronic apparatus 100 is received, so as to allow the electronic apparatus 100 to be easily drawn out from the charger 1340.

In response to the user pressing the physical button 1631 via pressure, the charger 1340 is opened by a predetermined angle as shown in FIG. 13E. Accordingly, the user can easily draw out the electronic apparatus 100 when the charger 1340 is opened by the predetermined angle. The charger 1340 may include an input terminal 1362 disposed in an inner space thereof, for charging the electronic apparatus 100. For example, the input terminal 1362 may matchingly connect with the wire communication terminal 580 described with reference to FIG. 5. Accordingly, in response to the electronic apparatus 100 being inserted into the charger 1340, pressed downwardly and fixed, the electronic apparatus 100 may be provided with power via the input terminal 1362 disposed in the inner space and may be charged.

Figure 13F:
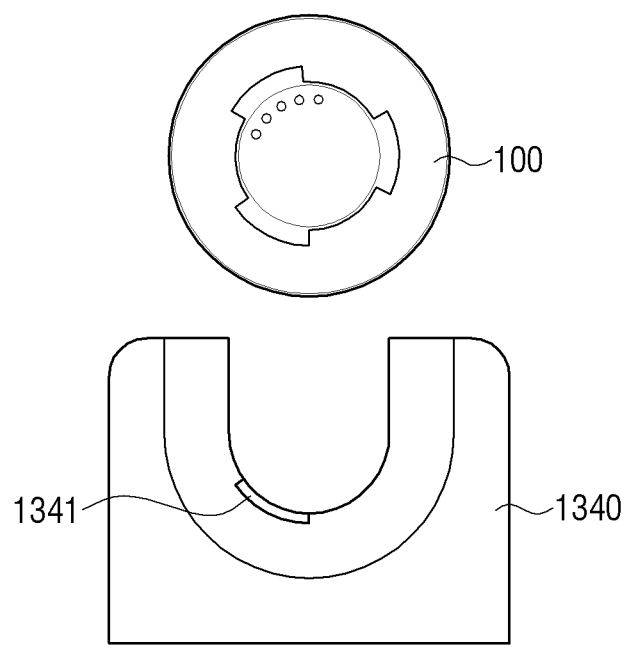

Referring to FIG. 13F, a groove 1341 of a predetermined size is formed in the charger 1340 to prevent the electronic apparatus 100 inserted into the charger 1340 from being rotated, and to fix the electronic apparatus 100. Accordingly, the electronic apparatus 100 inserted into the charger 1340 can be prevented from being rotated, disconnected from the input terminal 1362 disposed in the inner space, and released from the charging state.

Figure 13G:
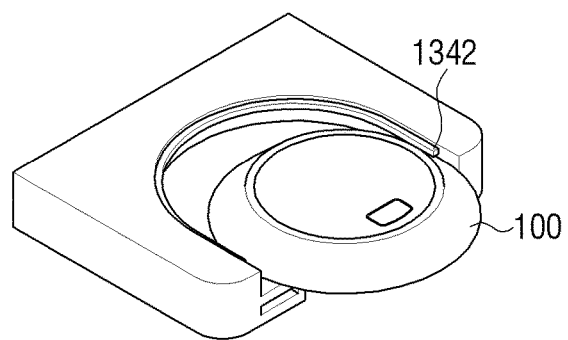

Referring to FIG. 13G, a guide line 1342 of a predetermined size is implemented in a physical structure to prevent the electronic apparatus 100 inserted into the charger 1340 from being released upwardly. Accordingly, the electronic apparatus 100 inserted into the charger 1340 can be prevented from being released upwardly by the guide line 1342.

Figure 13H:
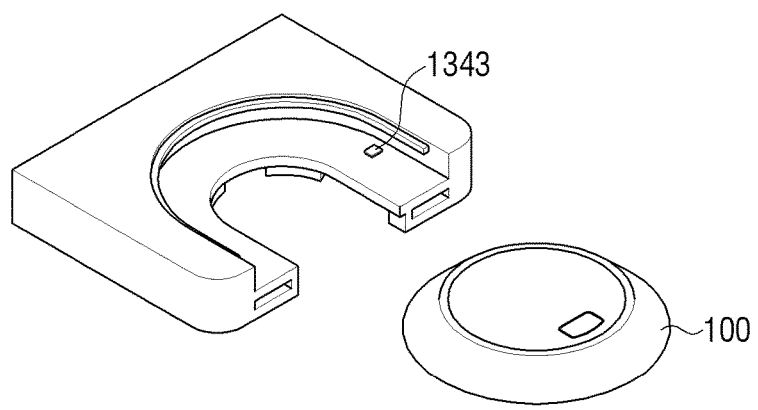

Referring to FIG. 13H, a protrusion 1343 may be disposed on a part of the inner area of the charger 1340 to fix the electronic apparatus 100. Accordingly, the electronic apparatus 100 can be prevented from being rotated and released by the protrusion 1343 included in the charger 1340. The protrusion 1343 may fix the electronic apparatus 100 by being implemented to be retracted and popped out via a spring formed therein.

Figure 13I:
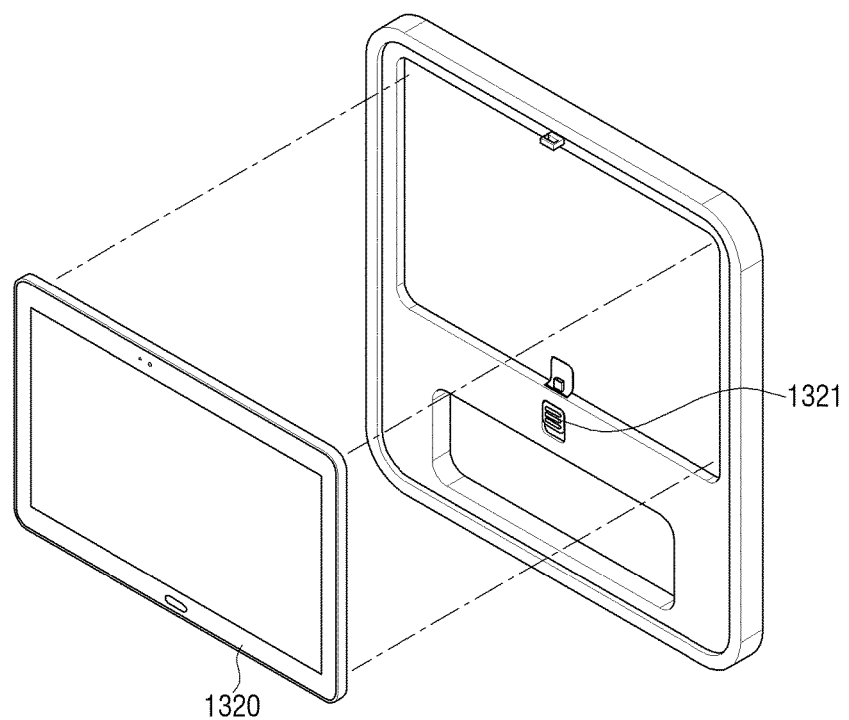

Referring to FIG. 13I, the tablet PC 1320 may be inserted into a groove formed on the cover of the upper end of the receiving box 1300 and attached thereto, and the tablet PC 1320 may be fixed and simultaneously may be connected with the receiving box 1300 in a wire communication method by sliding up a button 1321, which includes an interface for fixing the tablet PC 1320 and transmitting data between the tablet PC 1320 and the receiving box 1300.

Figure 13J:
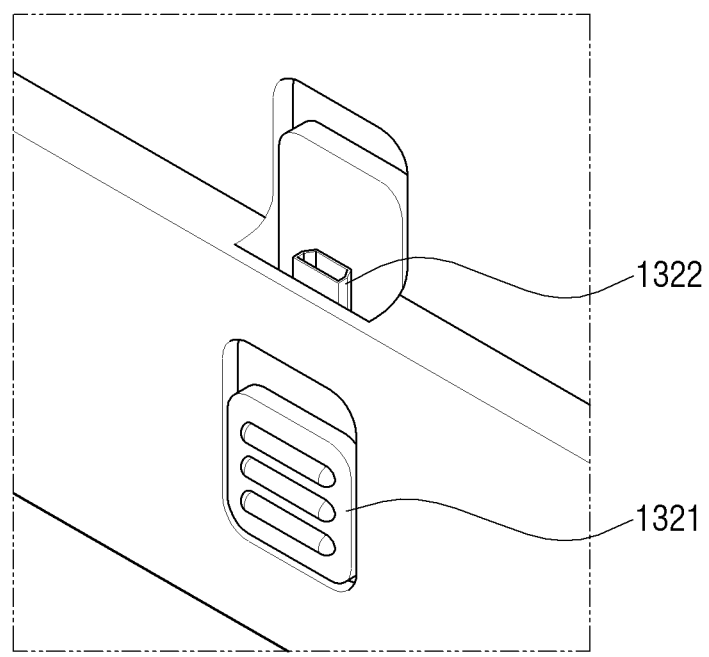

Specifically, referring to FIG. 13J, in response to the button 1321 sliding down, the button 1321 may be unlocked and thereby may hide the interface 1322 for transmitting data between the tablet PC 1320 and the receiving box 1300.

Figure 13K:
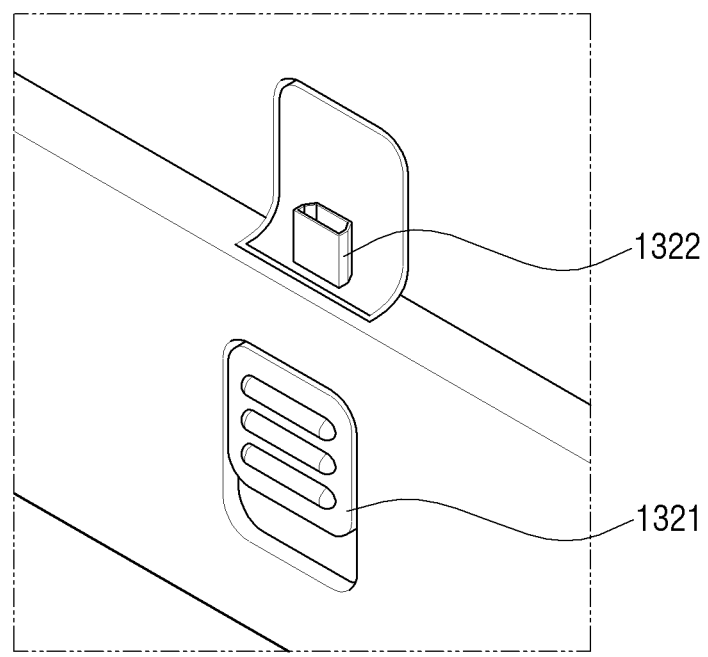

Referring to FIG. 13K, in response to the button 1321 sliding up, the button 1321 may be locked and thereby may eject the interface 1322 for transmitting data between the tablet PC 1320 and the receiving box 1300.

The tablet PC 1320 described above with reference to FIGS. 13A to 13K as the external apparatus 200 is merely an example and the external apparatus is not limited to the tablet PC 1320. The external apparatus may be implemented by using all kinds of electronic apparatuses which are cable of executing diagnosis-related software programs or applications, such as a smart phone, a PDA, a notebook PC, or the like.

According to an exemplary embodiment, various measurement modules are selectively attached to the electronic apparatus and used when needed, and the electronic apparatus includes common elements included in various measurement modules, such that a diagnostic device can be miniaturized and a price thereof can be reduced.

Figure 14:
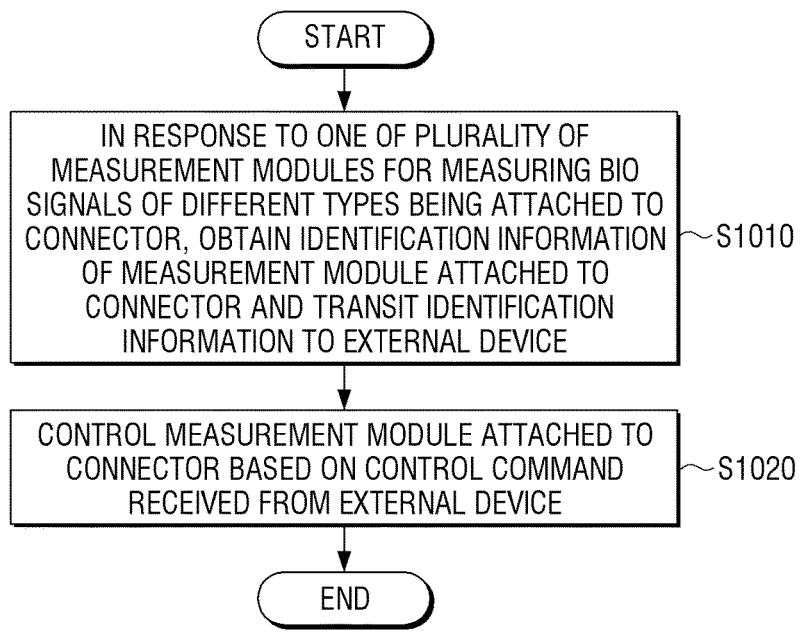
FIG. 14 is a flowchart to illustrate a control method of an electronic apparatus according to an exemplary embodiment.

FIG. 14 is a flowchart to illustrate a control method of an electronic apparatus according to an exemplary embodiment.

As shown in FIG. 14, a control method of an electronic apparatus including a connector, which is implemented to enable one of a plurality of measurement modules for measuring different types of bio signals to be selectively attached thereto and detached therefrom includes, in response to one of the plurality of measurement modules being attached to the connector, obtaining identification information of the measurement module attached to the connector and transmitting the identification information to an external apparatus (operation S1010).

The electronic apparatus controls the measurement module attached to the connector based on a control command received from the external apparatus (operation S1020).

Each of the plurality of measurement modules may include a different sensor according to a type of a bio signal to be measured.

The controlling may include, in response to a control command for starting measuring the bio signal being received from the external apparatus which has received an identification number of the measurement module attached to the connector, driving the measurement module attached to the connector and starting measuring the bio signal, and, in response to a control command for stopping measuring the bio signal being received from the external apparatus, driving the measurement module attached to the connector and stopping measuring the bio signal.

The controlling may include converting power charged in a battery included in the electronic apparatus into a driving voltage for the measurement module attached to the connector, and providing the driving voltage to the measurement module attached to the connector.

The transmitting may include, in response to the electronic apparatus and the external apparatus being adjacent to each other within a predetermined range, exchanging information for Bluetooth communication pairing with the external apparatus through NFC tagging, and, in response to the Bluetooth communication pairing being completed, transmitting the identification information of the measurement module attached to the connector to the external apparatus through the Bluetooth communication.

According to an exemplary embodiment, the control method of the electronic apparatus may further include displaying information on a state of the electronic apparatus.

The information on the state of the electronic apparatus may include at least one piece of information of information on an operation state of the electronic apparatus, an amount of power charged in a battery, and whether the battery is charged. For example, the operation state may indicate whether the measurement module is connected, which measurement module is connected, whether the measurement operation is in process, whether the measurement operation is pending, a degree of completion of the measurement operation, a time remaining until completion of the measurement operation, whether the measurement operation is completed, etc.

The connector may include a connection terminal for connecting with one of the plurality of measurement modules, and the control method may further include: transmitting the driving voltage of the measurement module attached to the connector and the control command to the measurement module attached to the connector via the connection terminal; and receiving information on the bio signal from the measurement module attached to the connector via the connection terminal.

The control method of the electronic apparatus according to various exemplary embodiments may be implemented as a program code executable by a computer, and may be stored in various non-transitory computer readable media and provided to each device to be executed by a controller.

For example, a non-transitory computer-readable medium which stores a program for performing a control method including: in response to one of the plurality of measurement modules being attached to the connector, obtaining identification information of the measurement module attached to the connector and transmitting the identification information to an external apparatus; and controlling the measurement module connected to the connector based on a control command received from the external apparatus, may be provided.

The non-transitory computer-readable medium refers to a medium that stores data semi-permanently rather than storing data for a very short time, such as a register, a cache, a memory or etc., and is readable by an apparatus. Specifically, the above-described various applications or programs may be stored in the non-transitory computer readable medium such as a compact disc (CD), a digital versatile disk (DVD), a hard disk, a Blu-ray disk, a universal serial bus (USB), a memory card, a ROM or etc., and may be provided In the above-described block diagrams showing the electronic apparatus, a bus is not illustrated. However, communication between the elements in the electronic apparatus may be performed through a bus. In addition, each of the apparatuses may further include a processor for performing the above-described various operations, such as a CPU, a microprocessor, etc.

The foregoing exemplary embodiments and advantages are merely exemplary and are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A user terminal apparatus comprising:
a communication interface configured to communicate with an external electronic apparatus which enables one of a plurality of measurement devices for measuring different types of bio signals to be selectively attached thereto or detached therefrom;
a display; and
a processor configured to:
based on receiving, from the external electronic apparatus via the communication interface, a first identification information of a first measurement device attached to the external electronic apparatus, execute software for driving the first measurement device based on the first identification information, and control the display to display a first user interface screen corresponding to the first measurement device that is generated using the software executed based on the first identification information,
based on receiving, from the external electronic apparatus via the communication interface, a second identification information of a second measurement device attached to the external electronic apparatus, execute software for driving the second measurement device based on the second identification information, and control the display to display a second user interface screen corresponding to the second measurement device that is generated using the software executed based on the second identification information, and
based on receiving a user input through the second user interface screen, transmit, via the communication interface, a control command for controlling the second measurement device based on the user input, to the external electronic apparatus,
wherein the processor is further configured to:
control the display to display a third user interface screen including a plurality of items corresponding to a plurality of medical conditions, respectively, and
based on receiving a user input to select one of the plurality of items through the third user interface screen, control the display to display guide information informing of at least one measurement device from among the plurality of measurement devices to measure a bio signal, among the bio signals, regarding one of the plurality of medical conditions corresponding to the one of the plurality of items that has been selected.

2. The user terminal apparatus of claim 1, wherein the at least one measurement device comprises the second measurement device, and
based on receiving, through the second user interface screen, a user input for starting measuring the bio signal, the processor is further configured to transmit, to the external electronic apparatus via the communication interface, a control command for driving the second measurement device to start the measuring the bio signal, and, based on receiving, through the second user interface screen, a user input for stopping the measuring the bio signal, the processor is further configured to transmit, to the external electronic apparatus via the communication interface, a control command for driving the second measurement device to stop the measuring the bio signal.

3. The user terminal apparatus of claim 1, wherein the communication interface comprises a near field communication (NFC) tagger and a Bluetooth communication device, and
the processor is further configured to exchange information for Bluetooth communication pairing with the external electronic apparatus via the NFC tagger.

4. The user terminal apparatus of claim 1, wherein the processor is further configured to control the display to highlight the one of the plurality of items that has been selected for diagnosing the one of the plurality of medical conditions.

5. The user terminal apparatus of claim 1, wherein the bio signal is a first bio signal, and the processor is further configured to control the display to display the guide information informing that both the first measurement device and the second measurement device are to be connected to the external electronic apparatus in a predetermined order, to measure the first bio signal and a second bio signal, respectively, based on the one of the plurality of items that has been selected, for diagnosing the one of the plurality of medical conditions.

6. A system comprising:

an electronic apparatus which enables one of a plurality of measurement devices for measuring different types of bio signals to be selectively attached thereto and detached therefrom, wherein the electronic apparatus comprises a first connection terminal configured to be electrically connected with a second connection terminal of the one of the plurality of measurement devices, and a communication device configured to communicate with external devices connected to the electronic apparatus via a network; and a user terminal configured to control the electronic apparatus, by communicating with the electronic apparatus via the communication device, wherein the electronic apparatus is configured to, based on a first measurement device of the plurality of measurement devices being connected, obtain a first identification information of the first measurement device via the first connection terminal and transmit the first identification information to the user terminal via the communication device, wherein the user terminal is further configured to, based on the first identification information being received from the electronic apparatus, execute software for driving the first measurement device based on the first identification information, and display a first user interface screen corresponding to the first measurement device that is generated using the software executed based on the first identification information, wherein the electronic apparatus is further configured to, based on the first measurement device being disconnected and a second measurement device of the plurality of measurement devices being connected, obtain, via the first connection terminal, a second identification information of the second measurement device and transmit, via the communication device, the second identification information to the user terminal, wherein the user terminal is further configured to, based on the second identification information being received from the electronic apparatus, execute software for driving the second measurement device based on the second identification information, display a second user interface screen corresponding to the second measurement device that is generated using the software executed based on the second identification information, and transmit a control command input by a user through the second user interface screen, to the electronic apparatus, wherein the electronic apparatus is further configured to, based on receiving the control command from the user terminal via the communication device, transmit data for controlling the second measurement device based on the control command, to the second measurement device via the first connection terminal, wherein the electronic apparatus provides power to the plurality of measurement devices at driving voltages, each of the driving voltages corresponding to each of the plurality of measurement devices, wherein the user terminal is further configured to:

display a third user interface screen including a plurality of items corresponding to a plurality of medical conditions, respectively, and based on receiving a user input to select one of the plurality of items through the third user interface screen, display guide information informing of at least one measurement device from among the plurality of measurement devices to measure a bio signal, among the bio signals, regarding one of the plurality of medical conditions corresponding to the one of the plurality of items that has been selected.

7. The system of claim 6, wherein the at least one measurement device comprises the second measurement device, and based on information on the bio signal measured by the second measurement device being received, the user terminal is further configured to analyze the received information on the bio signal and display a result of the analyzing on the second user interface screen.

8. A control method of a user terminal apparatus communicating with an external electronic apparatus which enables one of a plurality of measurement devices for measuring different types of bio signals to be selectively attached thereto and detached therefrom, the control method comprising:

based on receiving, from the external electronic apparatus, a first identification information of a first measurement device attached to the external electronic apparatus, executing software for driving the first measurement device based on the first identification information, and displaying a first user interface screen corresponding to the first measurement device that is generated using the software executed based on the first identification information;

based on receiving, from the external electronic apparatus, a second identification information of a second measurement device attached to the external electronic apparatus, executing software for driving the second measurement device based on the second identification information and displaying a second user interface screen corresponding to the second measurement device that is generated using the software executed based on the second identification information; and based on receiving a user input through the second user interface screen, transmitting a control command for controlling the second measurement device based on the user input, wherein the control method further comprises:

displaying a third user interface screen including a plurality of items corresponding to a plurality of medical conditions, respectively, and based on receiving a user input to select one of the plurality of items through the third user interface screen, displaying guide information informing of at least one measurement device from among the plurality of measurement devices to measure a bio signal, among the bio signals, regarding one of the plurality of medical conditions corresponding to the one of the plurality of items that has been selected.

9. The control method of claim 8, wherein the at least one measurement device comprises the second measurement device and the control method further comprises:

based on receiving, through the second user interface screen, a user input for starting measuring the bio signal, transmitting to the external electronic apparatus, a control command for driving the second measurement device to start the measuring the bio signal; and based on receiving, through the second user interface screen, a user input for stopping the measuring the bio signal, transmitting to the external electronic apparatus, a control command for driving the second measurement device to stop the measuring the bio signal.

10. The control method of claim 8, further comprising:

based on the external electronic apparatus and the user terminal apparatus being adjacent to each other within a certain range, exchanging information for Bluetooth communication pairing with the external electronic apparatus through a near field communication (NFC) tagging.

* * * * *